US012799169B2

(12) United States Patent
Fujinaga et al.

(10) Patent No.: US 12,799,169 B2
(45) Date of Patent: Nov. 17, 2026

(54) HEMAGGLUTININ COMPLEX PROTEIN AND APPLICATION THEREOF

(71) Applicant: OSAKA UNIVERSITY, Suita (JP)

(72) Inventors: Yukako Fujinaga, Kanazawa (JP); Sho Amatsu, Kanazawa (JP); Masahiro Kinooka, Suita (JP)

(73) Assignee: OSAKA UNIVERSITY, Suita (JP)

( * ) Notice: Subject to any disclaimer, the term of this patent is extended or adjusted under 35 U.S.C. 154(b) by 212 days.

(21) Appl. No.: 18/910,921

(22) Filed: Oct. 9, 2024

(65) Prior Publication Data

US 2025/0042954 A1 Feb. 6, 2025

Related U.S. Application Data

(62) Division of application No. 16/766,596, filed as application No. PCT/JP2018/043249 on Nov. 22, 2018, now Pat. No. 12,173,034.

(30) Foreign Application Priority Data

Nov. 24, 2017 (JP) ................................ 2017-226370

(51) Int. Cl.
*C07K 14/33* (2006.01)
*C12N 15/85* (2006.01)

(52) U.S. Cl.
CPC .............. *C07K 14/33* (2013.01); *C12N 15/85* (2013.01)

(58) Field of Classification Search
CPC ..... C07K 14/33; C07K 2319/00; C12N 15/85
See application file for complete search history.

(56) References Cited

U.S. PATENT DOCUMENTS

| | | | |
|---|---|---|---|
| 7,514,088 | B2 | 4/2009 | Steward |
| 11,230,701 | B2 | 1/2022 | Kinooka et al. |
| 2014/0235836 | A1 | 8/2014 | Song et al. |
| 2015/0329831 | A1 | 11/2015 | Kinooka et al. |
| 2017/0130206 | A1 | 5/2017 | Kinooka et al. |

FOREIGN PATENT DOCUMENTS

| | | | |
|---|---|---|---|
| CA | 2953670 | A1 | 12/2015 |
| EP | 3 153 175 | A1 | 4/2017 |
| WO | 2014/104207 | A1 | 7/2014 |
| WO | 2015/199243 | A1 | 12/2015 |
| WO | PCT/JP2018/043249 | | 11/2018 |

OTHER PUBLICATIONS

Kwangkook Lee et al., "Structure of a Bimodular Botulinum Neurotoxin Complex Provides Insights into Its Oral Toxicity", PLOS/PATHOGENS, Oct. 2013, pp. 1-13, vol. 9, Issue 10, Article e1003690.

International Search Report for PCT/JP2018/043249, dated Feb. 5, 2019.

Sugawara et al., "Functional Dissection of the Clostridium botulinum Type B Hemagglutinin Complex: Identification of the Carbohydrate and E-Cadherin Binding Sites", Plos One, Oct. 2014, vol. 9, Issue 10, e111170 (9 pages).

Supplementary European Search Report dated Jul. 30, 2021 in Application No. EP 18 88 0123.

Jin et al., "Disruption of the epithelial barrier by botulinum haemagglutinin (HA) proteins—differences in cell tropism and the mechanism of action between HA proteins of types A or B, and HA proteins of type C", Microbiology, vol. 155, pp. 35-45, 2009 (11 pages total).

Matsumura et al., "The HA proteins of botulinum toxin disrupt intestinal epithelial intercellular junctions to increase toxin absorption", Cellular Microbiology, vol. 10, No. 2, pp. 355-364, 2008 (10 pages total).

Sugawara et al., "Botulinum hemagglutinin disrupts the intercellular epithelial barrier by directly binding E-cadherin", J. Cell. Biol. vol. 189, No. 4, pp. 691-700, 2010 (10 pages total).

Amatsu et al., "Crystal Structure of Clostridium botulinum Whole Hemagglutinin Reveals a Huge Triskelion-shaped Molecular Complex", The Journal of Biological Chemistry, vol. 288, No. 49, pp. 35617-35625, Dec. 6, 2013 (10 pages total).

Lee et al., "Molecular basis for disruption of E-cadherin adhesion by botulinum neurotoxin A complex", Science, vol. 344, No. 6190, pp. 1405-1410, Jun. 20, 2014 (11 pages total).

U.S. Appl. No. 16/766,596, filed May 22, 2020.

*Primary Examiner* — Ganapathirama Raghu
(74) *Attorney, Agent, or Firm* — Sughrue Mion, PLLC

(57) ABSTRACT

A nucleic acid encoding a miniaturized hemagglutinin complex protein, wherein the miniaturized hemagglutinin complex protein has function inhibitory activity against E-cadherin, and wherein the miniaturized hemagglutinin complex protein is selected from the group consisting of: (1) mini-HA consisting of HA1 subcomponent of SEQ ID NO: 10, HA2 subcomponent of SEQ ID NO: 4, and HA3 subcomponent fragment of SEQ ID NO: 2, (2) FL(2+3)-C consisting of HA2 subcomponent of SEQ ID NO: 4 and HA3 component with Strep-Tag (C-terminus) of SEQ ID NO: 44, (3) linked-mini(2+3)/BB of SEQ ID NO: 47, (4) linked-mini(2+3)/CB of SEQ ID NO: 48, (5) linked-mini(2+3)/CB-YFDY of SEQ ID NO: 49, and (6) linked-mini(2+3)/CB-LD/YFDY of SEQ ID NO: 50.

2 Claims, 12 Drawing Sheets

Specification includes a Sequence Listing.

Amino acid sequence of nano-HA (linked-mini(2+3)/CB-LD-YFDY)

SEQUENCE LISTING

```
Sequence total quantity: 52
SEQ ID NO: 1            moltype = AA  length = 247
FEATURE                 Location/Qualifiers
source                  1..247
                        mol_type = protein
                        note = Clostridium botulinum type A
                        organism = Clostridium botulinum
```

-continued

```
SEQUENCE: 1
ENIQEINTAI SDNYTYNIPG IVNNNPFYIL FTVNTTGIYK INAQNNLPSL KIYEAIGSGN  60
RNFQSGNLCD DDIKAINYIT GFDSPNAKSY LVVLLNKDKN YYIRVPQTSS NIENQIQFKR  120
EEGDLRNLMN SSVNIIDNLN STGAHYYTRQ SPDVHDYISY EFTIPGNFNN KDTSNIRLYT  180
SYNQGIGTLF RVTETIDGYN LINIQQNLHL LNNTNSIRLL NGAIYILKVE VTELNNYNIR  240
LHIDITN                                                           247

SEQ ID NO: 2           moltype = AA  length = 247
FEATURE                Location/Qualifiers
source                 1..247
                       mol_type = protein
                       note = Clostridium botulinum typeB
                       organism = Clostridium botulinum
SEQUENCE: 2
ENIQEINTAI SDNYTYNIPG IVNNNPFYIL FTVNTTGIYK INAQNNLPSL KIYEAIGSGN  60
RNFQSGNLCD DDIKAINYIT GFDSPNAKSY LVVLLNKDKN YYIRVPQTSS NIENQIKFKR  120
EEGDLRNLMN SSVNIIDNLN STGAHYYTRQ SPDVHDYISY EFTIPGNFNN KDTSNIRLYT  180
SYNQGIGTLF RVTETIDGYN LINIQQNLNL LNSTKSIRLL NGAIYILKVE VTELNNYNIK  240
LHIDITN                                                           247

SEQ ID NO: 3           moltype = AA  length = 146
FEATURE                Location/Qualifiers
source                 1..146
                       mol_type = protein
                       note = Clostridium botulinum type A
                       organism = Clostridium botulinum
SEQUENCE: 3
MSVERTFLPN GNYNIKSIFS GSLYLNPVSK SLTFSNESSA NNQKWNVEYM AENRCFKISN  60
VAEPNKYLSY DNFGFISLDS LSNRCYWFPI KIAVNTYIML SLNKVNELDY AWDIYDTNEN  120
ILSQPLLLLP NFDIYNSNQM FKLEKI                                      146

SEQ ID NO: 4           moltype = AA  length = 146
FEATURE                Location/Qualifiers
source                 1..146
                       mol_type = protein
                       note = Clostridium botulinum type B
                       organism = Clostridium botulinum
SEQUENCE: 4
MSAERTFLPN GNYNIKSIFS GSLYLSPVSG SLTFSNESSA NNQKWNVEYM AENRCFKISN  60
VAEPNKYLSY DNFGFISLDS LSNRCYWFPI KIAVNTYIML SLNKVNELDY AWDIYDTNEN  120
ILSQPLLLLP NFDIYNSNQM FKLEKI                                      146

SEQ ID NO: 5           moltype = AA  length = 146
FEATURE                Location/Qualifiers
source                 1..146
                       mol_type = protein
                       note = Clostridium botulinum type C
                       organism = Clostridium botulinum
SEQUENCE: 5
MSSERTFLPN GNYKIKSLFS DSLYLTYSSG ALSFSNTSSL DNQKWKLEYI SSSNGFRFSN  60
VAEPNKYLAY NDYGFIYLSS SSNNSLWNPI KIAINSYIIC TLSIVNVTDY AWTIYDNNNN  120
ITDQPILNLP NFDINNSNQI LKLEKL                                      146

SEQ ID NO: 6           moltype = AA  length = 146
FEATURE                Location/Qualifiers
source                 1..146
                       mol_type = protein
                       note = Clostridium phage D-1873
                       organism = unidentified
SEQUENCE: 6
MSSERTFLPN GNYKIKSLFS NSLYLTYSSG ALSFSNTSSL DNQKWKLEYI SSSNGFRFSN  60
VAEPNKYLAY NDYGFIYLSS SSNNSLWNPI KIAINSYIIC TLSIVNVTDY AWTIYDNNNN  120
ITDQPILNLP NFDINNSNQI LKLEKL                                      146

SEQ ID NO: 7           moltype = AA  length = 626
FEATURE                Location/Qualifiers
source                 1..626
                       mol_type = protein
                       note = Clostridium botulinum type A
                       organism = Clostridium botulinum
SEQUENCE: 7
MNSSIKKIYN DIQEKVINYS DTIDLADGNY VVRRGDGWIL SRQNQILGGS VISNGSTGIV  60
GDLRVNDNAI PYYYPTPSFN EEYIKNNIQT VFTNFTEANQ IPIGFEFSKT APSNKNLYMY  120
LQYTYIRYEI IKVLQHEIIE RAVLYVPSLG YVKSIEFNPG EKINKDFYFL TNDKCILNEQ  180
FLYKKILETT KNIPTNNIFN SKVSSTQRVL PYSNGLYVIN KGDGYIRTND KDLIGTLLIE  240
AGSSGSIIQP RLRNTTRPLF TTSNDTKFSQ QYTEERLKDA FNVQLFNTST SLFKFVEEAP  300
SDKNICIKAY NTYEKYELID YQNGSIVNKA EYYLPSLGYC EVTNAPSPES EVVKMQVAED  360
GFIQNGPEEE IVVGVIDPSE NIQEINTAIS DNYTYNIPGI VNNNPFYILF TVNTTGIYKI  420
NAQNNLPSLK IYEAIGSGNR NFQSGNLCDD DIKAINYITG FDSPNAKSYL VVLLNKDKNY  480
```

```
YIRVPQTSSN IENQIQFKRE EGDLRNLMNS SVNIIDNLNS TGAHYYTRQS PDVHDYISYE  540
FTIPGNFNNK DTSNIRLYTS YNQGIGTLFR VTETIDGYNL INIQQNLHLL NNTNSIRLLN  600
GAIYILKVEV TELNNYNIRL HIDITN                                       626

SEQ ID NO: 8           moltype = AA  length = 626
FEATURE                Location/Qualifiers
source                 1..626
                       mol_type = protein
                       note = Clostridium botulinum type B
                       organism = Clostridium botulinum
SEQUENCE: 8
MNSSIKKIYN HIQEKVINYS DTIDLADGNY VVSRGDGWIL SRQNQILGGS VISNGSTGIV  60
GDLRVNDNAI PYYYPTPSFN EEYIKNNIQT VFANFTEANQ IPIGFEFSKT APSNKNLYMY  120
LQYTYIRYEI IKVLQHEIIE RAVLYVPSLG YVKSIEFNPG EKINKDFYFL TNDKCILNEQ  180
FLYKKILETT KNIPTNNIFN SKVSSTQRVL PYSNGLYVIN KGDGYIRTND KDLIGTLLIE  240
AGSSGSIIQP RLRNTTRPLF TTSNDAKFSQ QYTEERLKDA FNVQLFNTST SLFKFVEEAP  300
SNKNICIKAY NTYEKYELID YQNGSIVNKA EYYLPSLGYC EVTNAPSPES EVVKTQVAED  360
GFIQNGPEEE IVVGVIDPSE NIQEINTAIS DNYTYNIPGI VNNNPFYILF TVNTTGIYKI  420
NAQNNLPSLK IYEAIGSGNR NFQSGNLCDD DIKAINYITG FDSPNAKSYL VVLLNKDKNY  480
YIRVPQTSSN IENQIKFKRE EGDLRNLMNS SVNIIDNLNS TGAHYYTRQS PDVHDYISYE  540
FTIPGNFNNK DTSNIRLYTS YNQGIGTLFR VTETIDGYNL INIQQNLNLL NSTKSIRLLN  600
GAIYILKVEV TELNNYNIKL HIDITN                                       626

SEQ ID NO: 9           moltype = AA  length = 293
FEATURE                Location/Qualifiers
source                 1..293
                       mol_type = protein
                       note = Clostridium botulinum type A
                       organism = Clostridium botulinum
SEQUENCE: 9
MEHYSVIQNS LNDKIVTISC KADTNLFFYQ VAGNVSLFQQ TRNYLERWRL IYDSNKAAYK  60
IKSMDIHNTN LVLTWNAPTH NISTQQDSNA DNQYWLLLKD IGNNSFIIAS YKNPNLVLYA  120
DTVARNLKLS TLNNSNYIKF IIEDYIISDL NNFTCKISPI LDLNKVVQQV DVTNLNVNLY  180
TWDYGRNQKW TIRYNEEKAA YQFFNTILSN GVLTWIFSNG NTVRVSSSND QNNDAQYWLI  240
NPVSDTDETY TITNLRDTTK ALDLYGGQTA NGTAIQVFNY HGDDNQKWNI RNP          293

SEQ ID NO: 10          moltype = AA  length = 294
FEATURE                Location/Qualifiers
source                 1..294
                       mol_type = protein
                       note = Clostridium botulinum type B
                       organism = Clostridium botulinum
SEQUENCE: 10
MEHYSTIQNS LNDKIVTISC KANTDLFFYQ VPGNGNVSLF QQTRNYLERW RIIYDSNKAA  60
YKIKSMNIYN TNLVLTWNAP THNISAQQDS NADNQYWLLL KDIGNNSFII ASYKNPNLVL  120
YADTVARNLK LSTLNNSSYI KFIIEDYVIS DFKNFTCRIS PILAGGKVVQ QVSMTNLAVN  180
LYIWNNDLNQ KWTIIYNEEK AAYQFFNKIL SNGVLTWIFS DGNTVRVSSS AQNNDAQYWL  240
INPVSDNYDR YTITNLRDKT KVLDLYGGQT ADGTTIQVFN SNGGDNQIWT MSNP         294

SEQ ID NO: 11          moltype = AA  length = 286
FEATURE                Location/Qualifiers
source                 1..286
                       mol_type = protein
                       note = Clostridium botulinum type C
                       organism = Clostridium botulinum
SEQUENCE: 11
MSQTNANDLR NNEVFFISPS NNTNKVLDKI SQSEVKLWNK LSGANQKWRL IYDTNKQAYK  60
IKVMDNTSLI LTWNAPLSSV SVKTDTNGDN QYWYLLQNYI SRNVIIRNYM NPNLVLQYNI  120
DDTLMVSTQT SSSNQFFKFS NCIYEALNNR NCKLQTQLNS DRFLSKNLNS QIIVLWQWFD  180
SSRQKWIIEY NETKSAYTLK CQENNRYLTW IQNSNNYVET YQSTDSLIQY WNINYLDNDA  240
SKYILYNLQD TNRVLDVYNS QIANGTHVIV DSYHGNTNQQ WIINLI                 286

SEQ ID NO: 12          moltype = AA  length = 285
FEATURE                Location/Qualifiers
source                 1..285
                       mol_type = protein
                       note = Clostridium phage D-1873
                       organism = unidentified
SEQUENCE: 12
MSQTNANDLR NNEVFFISPS NNTNKVLDKI SQSEVKLWNK LSGANQKWRL IYDTNKQAYK  60
IKVMDNTSLI LTWNAPLSSV SVKTDTNGDN QYWYLLQNYI SRNVIIRNYM NPNLVLQYNI  120
DDTLMVSTQT SSSNQFFKFS NCIYESFNNS TCKIQTSLTI KFIDKNQNSN NVTIWSWNNG  180
DNQKWKILYN ESKMAYTLTC IKNNEYLTWF SSIGNNVGTY RTEGNNDQYW FINYLNNDAS  240
MYTISNFSNQ SKFLDVVNSG LADGTNVQVW DSNGTSAQKW IITRL                  285

SEQ ID NO: 13          moltype = AA  length = 9
FEATURE                Location/Qualifiers
REGION                 1..9
                       note = Synthetic sequence, linker peptide
```

```
source                  1..9
                        mol_type = protein
                        organism = synthetic construct
SEQUENCE: 13
GSGGDDPPG                                                            9

SEQ ID NO: 14           moltype = DNA  length = 72
FEATURE                 Location/Qualifiers
misc_feature            1..72
                        note = Synthetic sequence, primer
source                  1..72
                        mol_type = other DNA
                        organism = synthetic construct
SEQUENCE: 14
taccatggct agcgcaagct acggatccgg tagtgcatgg agccacccgc agttcgaaaa  60
gtaagtcgac gc                                                       72

SEQ ID NO: 15           moltype = DNA  length = 72
FEATURE                 Location/Qualifiers
misc_feature            1..72
                        note = Synthetic sequence, primer
source                  1..72
                        mol_type = other DNA
                        organism = synthetic construct
SEQUENCE: 15
gcgtcgactt acttttcgaa ctgcgggtgg ctccatgcac taccggatcc gtagcttgcg  60
ctagccatgg ta                                                       72

SEQ ID NO: 16           moltype = DNA  length = 30
FEATURE                 Location/Qualifiers
misc_feature            1..30
                        note = Synthetic sequence, primer
source                  1..30
                        mol_type = other DNA
                        organism = synthetic construct
SEQUENCE: 16
ctagctagca tccaaaattc attaaatgac                                    30

SEQ ID NO: 17           moltype = DNA  length = 57
FEATURE                 Location/Qualifiers
misc_feature            1..57
                        note = Synthetic sequence, primer
source                  1..57
                        mol_type = other DNA
                        organism = synthetic construct
SEQUENCE: 17
cgggatcctt acttgtcgtc atcgtctttg tagtctgggt tactcatagt ccatatc     57

SEQ ID NO: 18           moltype = DNA  length = 31
FEATURE                 Location/Qualifiers
misc_feature            1..31
                        note = Synthetic sequence, primer
source                  1..31
                        mol_type = other DNA
                        organism = synthetic construct
SEQUENCE: 18
ctagctagct cagctgaaag aacttttcta c                                  31

SEQ ID NO: 19           moltype = DNA  length = 36
FEATURE                 Location/Qualifiers
misc_feature            1..36
                        note = Synthetic sequence, primer
source                  1..36
                        mol_type = other DNA
                        organism = synthetic construct
SEQUENCE: 19
ccgctcgagt tatatttttt caagtttgaa catttg                             36

SEQ ID NO: 20           moltype = DNA  length = 31
FEATURE                 Location/Qualifiers
misc_feature            1..31
                        note = Synthetic sequence, primer
source                  1..31
                        mol_type = other DNA
                        organism = synthetic construct
SEQUENCE: 20
gaaaaagggt accaatatag tgatactatt g                                  31

SEQ ID NO: 21           moltype = DNA  length = 31
```

```
FEATURE                 Location/Qualifiers
misc_feature            1..31
                        note = Synthetic sequence, primer
source                  1..31
                        mol_type = other DNA
                        organism = synthetic construct
SEQUENCE: 21
cgtgtcgact taattagtaa tatctatatg c                                31

SEQ ID NO: 22           moltype = DNA  length = 39
FEATURE                 Location/Qualifiers
misc_feature            1..39
                        note = Synthetic sequence, primer
source                  1..39
                        mol_type = other DNA
                        organism = synthetic construct
SEQUENCE: 22
gcgctagcaa tatagtgata ctattgattt agctgatgg                        39

SEQ ID NO: 23           moltype = DNA  length = 42
FEATURE                 Location/Qualifiers
misc_feature            1..42
                        note = Synthetic sequence, primer
source                  1..42
                        mol_type = other DNA
                        organism = synthetic construct
SEQUENCE: 23
ccggatccat tagtaatatc tatatgcaat tttatattat ag                    42

SEQ ID NO: 24           moltype = DNA  length = 48
FEATURE                 Location/Qualifiers
misc_feature            1..48
                        note = Synthetic sequence, primer
source                  1..48
                        mol_type = other DNA
                        organism = synthetic construct
SEQUENCE: 24
ggggtgatga ccctccagga tcagctgaaa gaacttttct acctaatg              48

SEQ ID NO: 25           moltype = DNA  length = 36
FEATURE                 Location/Qualifiers
misc_feature            1..36
                        note = Synthetic sequence, primer
source                  1..36
                        mol_type = other DNA
                        organism = synthetic construct
SEQUENCE: 25
actaccggat cctatttttt caagtttgaa catttg                          36

SEQ ID NO: 26           moltype = DNA  length = 26
FEATURE                 Location/Qualifiers
misc_feature            1..26
                        note = Synthetic sequence, primer
source                  1..26
                        mol_type = other DNA
                        organism = synthetic construct
SEQUENCE: 26
taagaaggag atataccatg gctagc                                      26

SEQ ID NO: 27           moltype = DNA  length = 53
FEATURE                 Location/Qualifiers
misc_feature            1..53
                        note = Synthetic sequence, primer
source                  1..53
                        mol_type = other DNA
                        organism = synthetic construct
SEQUENCE: 27
gggtcatcac ccccacttcc attagtaata tctatatgca attttatatt ata        53

SEQ ID NO: 28           moltype = DNA  length = 42
FEATURE                 Location/Qualifiers
misc_feature            1..42
                        note = Synthetic sequence, primer
source                  1..42
                        mol_type = other DNA
                        organism = synthetic construct
SEQUENCE: 28
gcgctagcga aaatatacaa gaaataaata ctgctatttc ag                    42
```

```
SEQ ID NO: 29          moltype = DNA  length = 31
FEATURE                Location/Qualifiers
misc_feature           1..31
                       note = Synthetic sequence, primer
source                 1..31
                       mol_type = other DNA
                       organism = synthetic construct
SEQUENCE: 29
ctagctagct caagtgaaag aacctttta c                                31

SEQ ID NO: 30          moltype = DNA  length = 37
FEATURE                Location/Qualifiers
misc_feature           1..37
                       note = Synthetic sequence, primer
source                 1..37
                       mol_type = other DNA
                       organism = synthetic construct
SEQUENCE: 30
acgcgtcgac ttaaagtttt tctaatttta aaatttg                         37

SEQ ID NO: 31          moltype = DNA  length = 48
FEATURE                Location/Qualifiers
misc_feature           1..48
                       note = Synthetic sequence, primer
source                 1..48
                       mol_type = other DNA
                       organism = synthetic construct
SEQUENCE: 31
ggggtgatga ccctccagga tcaagtgaaa gaaccttttt acctaatg             48

SEQ ID NO: 32          moltype = DNA  length = 41
FEATURE                Location/Qualifiers
misc_feature           1..41
                       note = Synthetic sequence, primer
source                 1..41
                       mol_type = other DNA
                       organism = synthetic construct
SEQUENCE: 32
actaccggat ccaagttttt ctaattttaa aatttgatta g                    41

SEQ ID NO: 33          moltype = DNA  length = 43
FEATURE                Location/Qualifiers
misc_feature           1..43
                       note = Synthetic sequence, primer
source                 1..43
                       mol_type = other DNA
                       organism = synthetic construct
SEQUENCE: 33
atgatgatgg ttatatctat ttaagttcat catctaataa tag                  43

SEQ ID NO: 34          moltype = DNA  length = 40
FEATURE                Location/Qualifiers
misc_feature           1..40
                       note = Synthetic sequence, primer
source                 1..40
                       mol_type = other DNA
                       organism = synthetic construct
SEQUENCE: 34
agatataacc atcatcatta taagctaaat atttattagg                      40

SEQ ID NO: 35          moltype = DNA  length = 38
FEATURE                Location/Qualifiers
misc_feature           1..38
                       note = Synthetic sequence, primer
source                 1..38
                       mol_type = other DNA
                       organism = synthetic construct
SEQUENCE: 35
aatccttgta aaattgctat aaattcttat attatatg                        38

SEQ ID NO: 36          moltype = DNA  length = 32
FEATURE                Location/Qualifiers
misc_feature           1..32
                       note = Synthetic sequence, primer
source                 1..32
                       mol_type = other DNA
                       organism = synthetic construct
SEQUENCE: 36
aattttacaa ggattccata aactattatt ag                              32
```

```
SEQ ID NO: 37          moltype = DNA  length = 32
FEATURE                Location/Qualifiers
misc_feature           1..32
                       note = Synthetic sequence, primer
source                 1..32
                       mol_type = other DNA
                       organism = synthetic construct
SEQUENCE: 37
agagtctgtg aaactattga cggctataat tt                          32

SEQ ID NO: 38          moltype = DNA  length = 32
FEATURE                Location/Qualifiers
misc_feature           1..32
                       note = Synthetic sequence, primer
source                 1..32
                       mol_type = other DNA
                       organism = synthetic construct
SEQUENCE: 38
agtttcacag actctaaata aagtacctat tc                          32

SEQ ID NO: 39          moltype = DNA  length = 31
FEATURE                Location/Qualifiers
misc_feature           1..31
                       note = Synthetic sequence, primer
source                 1..31
                       mol_type = other DNA
                       organism = synthetic construct
SEQUENCE: 39
tcttctgatg ataatcaaaa atggaagtta g                           31

SEQ ID NO: 40          moltype = DNA  length = 35
FEATURE                Location/Qualifiers
misc_feature           1..35
                       note = Synthetic sequence, primer
source                 1..35
                       mol_type = other DNA
                       organism = synthetic construct
SEQUENCE: 40
attatcatca gaagatgtat ttgaaaatga taatg                       35

SEQ ID NO: 41          moltype = AA  length = 319
FEATURE                Location/Qualifiers
REGION                 1..319
                       note = Synthetic sequence, His-BHA1-Flag
source                 1..319
                       mol_type = protein
                       organism = synthetic construct
SEQUENCE: 41
MGSSHHHHHH SSGLVPRGSH MASIQNSLND KIVTISCKAN TDLFFYQVPG NGNVSLFQQT  60
RNYLERWRII YDSNKAAYKI KSMNIYNTNL VLTWNAPTHN ISAQQDSNAD NQYWLLLKDI  120
GNNSFIIASY KNPNLVLYAD TVARNLKLST LNNSSYIKFI IEDYVISDFK NFTCRISPIL  180
AGGKVVQQVS MTNLAVNLYI WNNDLNQKWT IIYNEEKAAY QFFNKILSNG VLTWIFSDGN  240
TVRVSSSAQN NDAQYWLINP VSDNYDRYTI TNLRDKTKVL DLYGGQTADG TTIQVFNSNG  300
GDNQIWTMSN PDYKDDDDK                                          319

SEQ ID NO: 42          moltype = AA  length = 168
FEATURE                Location/Qualifiers
REGION                 1..168
                       note = Synthetic sequence, His-BHA2
source                 1..168
                       mol_type = protein
                       organism = synthetic construct
SEQUENCE: 42
MGSSHHHHHH SSGLVPRGSH MASSAERTFL PNGNYNIKSI FSGSLYLSPV SGSLTFSNES  60
SANNQKWNVE YMAENRCFKI SNVAEPNKYL SYDNFGFISL DSLSNRCYWF PIKIAVNTYI  120
MLSLNKVNEL DYAWDIYDTN ENILSQPLLL LPNFDIYNSN QMFKLEKI          168

SEQ ID NO: 43          moltype = AA  length = 632
FEATURE                Location/Qualifiers
REGION                 1..632
                       note = Synthetic sequence, Strep-BHA3
source                 1..632
                       mol_type = protein
                       organism = synthetic construct
SEQUENCE: 43
MASWSHPQFE KGALEVLFQG PGYQYSDTID LADGNYVVSR GDGWILSRQN QILGGSVISN  60
GSTGIVGDLR VNDNAIPYYY PTPSFNEEYI KNNIQTVFAN FTEANQIPIG FEFSKTAPSN  120
KNLYMYLQYT YIRYEIIKVL QHEIIERAVL YVPSLGYVKS IEFNPGEKIN KDFYFLTNDK  180
```

```
CILNEQFLYK KILETTKNIP TNNIFNSKVS STQRVLPYSN GLYVINKGDG YIRTNDKDLI  240
GTLLIEAGSS GSIIQPRLRN TTRPLFTTSN DAKFSQQYTE ERLKDAFNVQ LFNTSTSLFK  300
FVEEAPSNKN ICIKAYNTYE KYELIDYQNG SIVNKAEYYL PSLGYCEVTN APSPESEVVK  360
TQVAEDGFIQ NGPEEEIVVG VIDPSENIQE INTAISDNYT YNIPGIVNNN PFYILFTVNT  420
TGIYKINAQN NLPSLKIYEA IGSGNRNFQS GNLCDDDIKA INYITGFDSP NAKSYLVVLL  480
NKDKNYYIRV PQTSSNIENQ IKFKREEGDL RNLMNSSVNI IDNLNSTGAH YYTRQSPDVH  540
DYISYEFTIP GNFNNKDTSN IRLYTSYNQG IGTLFRVTET IDGYNLINIQ QNLNLLNSTK  600
SIRLLNGAIY ILKVEVTELN NYNIKLHIDI TN                                632

SEQ ID NO: 44          moltype = AA  length = 624
FEATURE                Location/Qualifiers
REGION                 1..624
                       note = Synthetic sequence, BHA3-Strep
source                 1..624
                       mol_type = protein
                       organism = synthetic construct
SEQUENCE: 44
MASYSDTIDL ADGNYVVSRG DGWILSRQNQ ILGGSVISNG STGIVGDLRV NDNAIPYYYP  60
TPSFNEEYIK NNIQTVFANF TEANQIPIGF EFSKTAPSNK NLYMYLQYTY IRYEIIKVLQ  120
HEIIERAVLY VPSLGYVKSI EFNPGEKINK DFYFLTNDKC ILNEQFLYKK ILETTKNIPT  180
NNIFNSKVSS TQRVLPYSNG LYVINKGDGY IRTNDKDLIG TLLIEAGSSG SIIQPRLRNT  240
TRPLFTTSND AKFSQQYTEE RLKDAFNVQL FNTSTSLFKF VEEAPSNKNI CIKAYNTYEK  300
YELIDYQNGS IVNKAEYYLP SLGYCEVTNA PSPESEVVKT QVAEDGFIQN GPEEEIVVGV  360
IDPSENIQEI NTAISDNYTY NIPGIVNNNP FYILFTVNTT GIYKINAQNN LPSLKIYEAI  420
GSGNRNFQSG NLCDDDIKAI NYITGFDSPN AKSYLVVLLN KDKNYYIRVP QTSSNIENQI  480
KFKREEGDLR NLMNSSVNII DNLNSTGAHY YTRQSPDVHD YISYEFTIPG NFNNKDTSNI  540
RLYTSYNQGI GTLFRVTETI DGYNLINIQQ NLNLLNSTKS IRLLNGAIYI LKVEVTELNN  600
YNIKLHIDIT NGSGSAWSHP QFEK                                         624

SEQ ID NO: 45          moltype = AA  length = 778
FEATURE                Location/Qualifiers
REGION                 1..778
                       note = Synthetic sequence, linked-FL-HA(2+3)/B
source                 1..778
                       mol_type = protein
                       organism = synthetic construct
SEQUENCE: 45
MASYSDTIDL ADGNYVVSRG DGWILSRQNQ ILGGSVISNG STGIVGDLRV NDNAIPYYYP  60
TPSFNEEYIK NNIQTVFANF TEANQIPIGF EFSKTAPSNK NLYMYLQYTY IRYEIIKVLQ  120
HEIIERAVLY VPSLGYVKSI EFNPGEKINK DFYFLTNDKC ILNEQFLYKK ILETTKNIPT  180
NNIFNSKVSS TQRVLPYSNG LYVINKGDGY IRTNDKDLIG TLLIEAGSSG SIIQPRLRNT  240
TRPLFTTSND AKFSQQYTEE RLKDAFNVQL FNTSTSLFKF VEEAPSNKNI CIKAYNTYEK  300
YELIDYQNGS IVNKAEYYLP SLGYCEVTNA PSPESEVVKT QVAEDGFIQN GPEEEIVVGV  360
IDPSENIQEI NTAISDNYTY NIPGIVNNNP FYILFTVNTT GIYKINAQNN LPSLKIYEAI  420
GSGNRNFQSG NLCDDDIKAI NYITGFDSPN AKSYLVVLLN KDKNYYIRVP QTSSNIENQI  480
KFKREEGDLR NLMNSSVNII DNLNSTGAHY YTRQSPDVHD YISYEFTIPG NFNNKDTSNI  540
RLYTSYNQGI GTLFRVTETI DGYNLINIQQ NLNLLNSTKS IRLLNGAIYI LKVEVTELNN  600
YNIKLHIDIT NGSGGDDPPG SAERTFLPNG NYNIKSIFSG SLYLSPVSGS LTFSNESSAN  660
NQKWNVEYMA ENRCFKISNV AEPNKYLSYD NFGFISLDSL SNRCYWFPIK IAVNTYIMLS  720
LNKVNELDYA WDIYDTNENI LSQPLLLLPN FDIYNSNQMF KLEKIGSGSA WSHPQFEK    778

SEQ ID NO: 46          moltype = AA  length = 263
FEATURE                Location/Qualifiers
REGION                 1..263
                       note = Synthetic sequence, BHA3mini-Strep
source                 1..263
                       mol_type = protein
                       organism = synthetic construct
SEQUENCE: 46
MASENIQEIN TAISDNYTYN IPGIVNNNPF YILFTVNTTG IYKINAQNNL PSLKIYEAIG  60
SGNRNFQSGN LCDDDIKAIN YITGFDSPNA KSYLVVLLNK DKNYYIRVPQ TSSNIENQIK  120
FKREEGDLRN LMNSSVNIID NLNSTGAHYY TRQSPDVHDY ISYEFTIPGN FNNKDTSNIR  180
LYTSYNQGIG TLFRVTETID GYNLINIQQN LNLLNSTKSI RLLNGAIYIL KVEVTELNNY  240
NIKLHIDITN GSGSAWSHPQ FEK                                          263

SEQ ID NO: 47          moltype = AA  length = 417
FEATURE                Location/Qualifiers
REGION                 1..417
                       note = Synthetic sequence, linked-mini-HA(2+3)/B
source                 1..417
                       mol_type = protein
                       organism = synthetic construct
SEQUENCE: 47
MASENIQEIN TAISDNYTYN IPGIVNNNPF YILFTVNTTG IYKINAQNNL PSLKIYEAIG  60
SGNRNFQSGN LCDDDIKAIN YITGFDSPNA KSYLVVLLNK DKNYYIRVPQ TSSNIENQIK  120
FKREEGDLRN LMNSSVNIID NLNSTGAHYY TRQSPDVHDY ISYEFTIPGN FNNKDTSNIR  180
LYTSYNQGIG TLFRVTETID GYNLINIQQN LNLLNSTKSI RLLNGAIYIL KVEVTELNNY  240
NIKLHIDITN GSGGDDPPGS AERTFLPNGN YNIKSIFSGS LYLSPVSGSL TFSNESSANN  300
```

```
QKWNVEYMAE NRCFKISNVA EPNKYLSYDN FGFISLDSLS NRCYWFPIKI AVNTYIMLSL  360
NKVNELDYAW DIYDTNENIL SQPLLLLPNF DIYNSNQMFK LEKIGSGSAW SHPQFEK     417

SEQ ID NO: 48          moltype = AA  length = 417
FEATURE                Location/Qualifiers
REGION                 1..417
                       note = Synthetic sequence, linked-mini-HA(2+3)/CB
source                 1..417
                       mol_type = protein
                       organism = synthetic construct
SEQUENCE: 48
MASENIQEIN TAISDNYTYN IPGIVNNNPF YILFTVNTTG IYKINAQNNL PSLKIYEAIG  60
SGNRNFQSGN LCDDDIKAIN YITGFDSPNA KSYLVVLLNK DKNYYIRVPQ TSSNIENQIK  120
FKREEGDLRN LMNSSVNIID NLNSTGAHYY TRQSPDVHDY ISYEFTIPGN FNNKDTSNIR  180
LYTSYNQGIG TLFRVTETID GYNLINIQQN LNLLNSTKSI RLLNGAIYIL KVEVTELNNY  240
NIKLHIDITN GSGGDDPPGS SERTFLPNGN YKIKSLFSDS LYLTYSSGAL SFSNTSSLDN  300
QKWKLEYISS SNGFRFSNVA EPNKYLAYND YGFIYLSSSS NNSLWNPIKI AINSYIICTL  360
SIVNVTDYAW TIYDNNNNIT DQPILNLPNF DINNSNQILK LEKLGSGSAW SHPQFEK     417

SEQ ID NO: 49          moltype = AA  length = 417
FEATURE                Location/Qualifiers
REGION                 1..417
                       note = Synthetic sequence, linked-mini-HA(2+3)/CB-YFDY
source                 1..417
                       mol_type = protein
                       organism = synthetic construct
SEQUENCE: 49
MASENIQEIN TAISDNYTYN IPGIVNNNPF YILFTVNTTG IYKINAQNNL PSLKIYEAIG  60
SGNRNFQSGN LCDDDIKAIN YITGFDSPNA KSYLVVLLNK DKNYYIRVPQ TSSNIENQIK  120
FKREEGDLRN LMNSSVNIID NLNSTGAHYY TRQSPDVHDY ISYEFTIPGN FNNKDTSNIR  180
LYTSYNQGIG TLFRVTETID GYNLINIQQN LNLLNSTKSI RLLNGAIYIL KVEVTELNNY  240
NIKLHIDITN GSGGDDPPGS SERTFLPNGN YKIKSLFSDS LYLTYSSGAL SFSNTSSLDN  300
QKWKLEYISS SNGFRFSNVA EPNKYLAYND DGYIYLSSSS NNSLWNPIKI AINSYIICTL  360
SIVNVTDYAW TIYDNNNNIT DQPILNLPNF DINNSNQILK LEKLGSGSAW SHPQFEK     417

SEQ ID NO: 50          moltype = AA  length = 417
FEATURE                Location/Qualifiers
REGION                 1..417
                       note = Synthetic sequence, linked-mini-HA(2+3)/CB-LD-YFDY
source                 1..417
                       mol_type = protein
                       organism = synthetic construct
SEQUENCE: 50
MASENIQEIN TAISDNYTYN IPGIVNNNPF YILFTVNTTG IYKINAQNNL PSLKIYEAIG  60
SGNRNFQSGN LCDDDIKAIN YITGFDSPNA KSYLVVLLNK DKNYYIRVPQ TSSNIENQIK  120
FKREEGDLRN LMNSSVNIID NLNSTGAHYY TRQSPDVHDY ISYEFTIPGN FNNKDTSNIR  180
LYTSYNQGIG TLFRVTETID GYNLINIQQN LNLLNSTKSI RLLNGAIYIL KVEVTELNNY  240
NIKLHIDITN GSGGDDPPGS SERTFLPNGN YKIKSLFSDS LYLTYSSGAL SFSNTSSDDN  300
QKWKLEYISS SNGFRFSNVA EPNKYLAYND DGYIYLSSSS NNSLWNPIKI AINSYIICTL  360
SIVNVTDYAW TIYDNNNNIT DQPILNLPNF DINNSNQILK LEKLGSGSAW SHPQFEK     417

SEQ ID NO: 51          moltype = AA  length = 417
FEATURE                Location/Qualifiers
REGION                 1..417
                       note = Synthetic sequence, linked-mini-HA(2+3)/CB-IC
source                 1..417
                       mol_type = protein
                       organism = synthetic construct
SEQUENCE: 51
MASENIQEIN TAISDNYTYN IPGIVNNNPF YILFTVNTTG IYKINAQNNL PSLKIYEAIG  60
SGNRNFQSGN LCDDDIKAIN YITGFDSPNA KSYLVVLLNK DKNYYIRVPQ TSSNIENQIK  120
FKREEGDLRN LMNSSVNIID NLNSTGAHYY TRQSPDVHDY ISYEFTIPGN FNNKDTSNIR  180
LYTSYNQGIG TLFRVTETID GYNLINIQQN LNLLNSTKSI RLLNGAIYIL KVEVTELNNY  240
NIKLHIDITN GSGGDDPPGS SERTFLPNGN YKIKSLFSDS LYLTYSSGAL SFSNTSSLDN  300
QKWKLEYISS SNGFRFSNVA EPNKYLAYND YGFIYLSSSS NNSLWNPCKI AINSYIICTL  360
SIVNVTDYAW TIYDNNNNIT DQPILNLPNF DINNSNQILK LEKLGSGSAW SHPQFEK     417

SEQ ID NO: 52          moltype = AA  length = 417
FEATURE                Location/Qualifiers
REGION                 1..417
                       note = Synthetic sequence, linked-mini-HA(2+3)/CB-ITCC
source                 1..417
                       mol_type = protein
                       organism = synthetic construct
SEQUENCE: 52
MASENIQEIN TAISDNYTYN IPGIVNNNPF YILFTVNTTG IYKINAQNNL PSLKIYEAIG  60
SGNRNFQSGN LCDDDIKAIN YITGFDSPNA KSYLVVLLNK DKNYYIRVPQ TSSNIENQIK  120
FKREEGDLRN LMNSSVNIID NLNSTGAHYY TRQSPDVHDY ISYEFTIPGN FNNKDTSNIR  180
LYTSYNQGIG TLFRVCETID GYNLINIQQN LNLLNSTKSI RLLNGAIYIL KVEVTELNNY  240
```

-continued

| | | | | | | |
|---|---|---|---|---|---|---|
| NIKLHIDITN | GSGGDDPPGS | SERTFLPNGN | YKIKSLFSDS | LYLTYSSGAL | SFSNTSSLDN | 300 |
| QKWKLEYISS | SNGFRFSNVA | EPNKYLAYND | YGFIYLSSSS | NNSLWNPCKI | AINSYIICTL | 360 |
| SIVNVTDYAW | TIYDNNNNIT | DQPILNLPNF | DINNSNQILK | LEKLGSGSAW | SHPQFEK | 417 |

HEMAGGLUTININ COMPLEX PROTEIN AND APPLICATION THEREOF

CROSS REFERENCE TO RELATED APPLICATIONS

This application is a Divisional Application of U.S. patent application Ser. No. 16/766,596, filed May 22, 2020, which is a National Stage of International Application No. PCT/JP2018/043249 filed Nov. 22, 2018, claiming priority based on Japanese Patent Application No. 2017-226370 filed Nov. 24, 2017.

INCORPORATION BY REFERENCE OF SEQUENCE LISTING

The content of the electronically submitted sequence listing, file name:

Q302712_Sequence Listing (revised); size 71.9 KB; and date of creation: Oct. 12, 2024, filed herewith, is incorporated herein by reference in its entirety.

TECHNICAL FIELD

The present invention relates to a novel miniaturized hemagglutinin complex protein maintaining cadherin function inhibitory activity, and use thereof.

BACKGROUND ART

When cells deviated from an undifferentiated state (hereinafter to be also referred to as "deviated cells") are accidentally developed in the process of maintenance or amplification culture of pluripotent stem cells such as induced pluripotent stem cells (hereinafter to be also referred to as "iPS cells") and the like, the conversion of undifferentiated cells to deviated cells is further induced, the proliferation of undifferentiated cells is suppressed, and the undifferentiated state becomes difficult to maintain. Therefore, it is necessary to remove the colonies containing deviated cells; however, this work is performed by a pipetting operation under a microscope during subculturing, and involves complicated and skill-requiring procedures. While an automated device for the work has been developed, it has not yet been fully automated or spread, and a simple method for maintaining undifferentiated pluripotent stem cells (removal and/or suppression of development of deviated cells) has been demanded.

The present inventors have found that hemagglutinin, a component of the botulinum neurotoxin complex (hereinafter to be also referred to as "HA") specifically binds to the cell adhesion factor, E-cadherin, and inhibits its function, thereby disrupting the intercellular barrier function (non-patent documents 1-3). A method using this cadherin function inhibitory activity of HA for removing the deviated cells generated in the colonies of pluripotent stem cells and maintaining the undifferentiated state of the pluripotent stem cells has already been reported (patent documents 1 and 2).

HA is constituted of three different subcomponents of HA1 (also called HA33), HA2 (also called HA17) and HA3 (also called HA70) (constituted of HA1:HA2:HA3=6:3:3 stoichiometry), and has a triskelion-like conformation in which three arms composed of HA1 (dimer) and HA2 are bound to HA3 (non-patent document 4). To recombinantly produce the whole HA complex (FL-HA; see FIG. 1), therefore, a step of expressing and purifying respective subunit proteins, mixing and incubating the three to form a 12-mer having the above-mentioned conformation, and further purifying same is required. Thus practicalization involves problems in terms of time, labor, cost, and the like.

If HA complex can be miniaturized while maintaining the cadherin function inhibitory activity, the production step can be simplified and an HA complex easy to handle can be provided. Thus, it can be greatly expected as a tool for maintaining undifferentiated pluripotent stem cells. However, the research group of Jin et al. has reported that a miniaturized HA complex constituted of HA1 dimer, HA2 and HA3 fragments (consisting of Pro at position 378 to Asn at position 626) (mini-HA; see FIG. 1) binds to E-cadherin but does not have barrier disruption activity, and considers that HA needs to be polyvalent to achieve barrier disruption activity (non-patent documents 5 and 6).

DOCUMENT LIST

Patent Documents patent document 1: WO 2014/104207 patent document 2: WO 2015/199243

Non-Patent Documents non-patent document 1: Jin, Y. et al., Microbiology, 155:35-45 (2009)

non-patent document 2: Matsumura, T. et al., Cell Microbiol., 10:355-364 (2008)

non-patent document 3: Sugawara, Y. et al., J. Cell. Biol., 189:691-700 (2010)

non-patent document 4: Amatsu, S. et al., J. Biol. Chem., 288:35617-35625 (2013)

non-patent document 5: Lee, K. et al., PLOS Pathog., 9: e1003690 (2013)

non-patent document 6: Lee, K. et al., Science, 344:1405-1410 (2014)

SUMMARY OF INVENTION

Technical Problem

Therefore, the purpose of the present invention is to provide a novel miniaturized HA complex protein maintaining cadherin function inhibitory activity, and provide a convenient means of maintaining an undifferentiated state of pluripotent stem cells at a low cost using the protein.

Solution to Problem

In an attempt to achieve the above-mentioned goal, the present inventors have tried two types of HA miniaturization strategy.

Firstly, mini-HA complex (containing Glu at position 380 to Asn at position 626 as HA3 fragment) which is similar to the one produced by Jin et al. was investigated for the cadherin function inhibitory activity using the transepithelial electrical resistance (TER) in cultured cells as an index. Surprisingly, it was found that the mini-HA complex lowers TER like FL-HA and has cadherin function inhibitory activity (see FIG. 1, FIG. 2).

Secondly, since it was clear from the results of pull-down assay and crystal structure analysis that the HA region that contributes to the binding with E-cadherin is the HA2-HA3 connecting region (see, for example, non-patent documents 3 and 4), full-length HA2 and HA3 were respectively expressed, mixed, reconstituted into HA2:HA3=3:3 HA complex (FL(2+3)), and examined for TER in cultured cells. As a result, TER decreased and it was found that a trivalent complex maintains cadherin function inhibitory activity even in the absence of HA1 subcomponent (see FIG. 1, FIG. 3). Furthermore, it was clarified that even when HA2 and HA3 are expressed as a fusion protein via a linker (linked-FL(2+3)), the cadherin function inhibitory activity is maintained, and functional HA2:HA3=3:3 HA complex can be easily produced without mixing and incubating after once purifying each subcomponent.

Furthermore, the present inventors similarly deleted HA1 subcomponent and further tried to achieve miniaturization also in the above-mentioned first HA miniaturization strategy. However, the cadherin function inhibitory activity disappeared in a HA complex obtained by deleting HA1 subcomponent from mini-HA complex (mini(2+3)) (see FIG. 1, FIG. 3).

The HA subcomponents used heretofore were all derived from Clostridium botulinum type B. The present inventors replaced the HA2 subcomponent in the mini(2+3) complex with that derived from HA of Clostridium botulinum type C, which is known not to interact with E-cadherin or disrupt the intercellular barrier of the human intestinal epithelial cell line (mini(2+3)/CB). As a result, surprisingly, a decrease in TER was observed though temporarily and transient cadherin function inhibitory activity was shown (see FIG. 1, FIG. 4).

Then, similar to the case of the FL(2+3) complex, the present inventors expressed each of mini(2+3) and mini(2+3)/CB with HA2 and HA3 as fusion proteins (linked-mini(2+3)/BB, linked-mini(2+3)/CB, respectively). Cadherin function inhibitory activity was exhibited even when HA2 subcomponent of type B was used by linking with a linker (see FIG. 1, FIG. 5). When HA2 subcomponent of type C was used, the transient cadherin function inhibitory activity changed to sustained activity by linking with a linker (see FIG. 1, FIG. 6, FIG. 7).

Furthermore, the present inventors introduced a mutation that substitutes each of 1 to several hydrophobic amino acid residues exposed on the surface of the molecules of the above-mentioned linked-mini(2+3)/CB with more hydrophilic amino acids (linked-mini(2+3)/CB-YFDY, linked-mini(2+3)/CB-LD/YFDY). As a result, by introducing these mutations, the cadherin function inhibitory activity was further improved, and the activity similar to that of the mini-HA complex was exhibited (see FIG. 1, FIG. 7). In addition, it was also confirmed that these mutation-introduced miniaturized HA complexes showed about 10 times or more improved yield as compared to an FL-HA expression system obtained by respectively producing three full-length HA subcomponents, mixing and reconstituting the subcomponents.

The present inventors then investigated whether linked-mini(2+3)/CB-LD/YFDY can, like FL-HA, inhibit the cell-cell adhesion of iPS cells, and confirmed that it inhibits the cell-cell adhesion at a concentration of at least 50 nM (see FIGS. 16A and 16B). In addition, the linked-mini(2+3)/CB-LD/YFDY showed a cell proliferation promoting action equivalent to FL-HA at the same molar concentration, and about 3 times stronger cell proliferation promoting action than FL-HA in terms of weight/volume concentration per single arm (protomer).

The present inventors conducted further studies based on these findings, and completed the present invention.

Accordingly, the present invention provides the following.

[1] A miniaturized hemagglutinin complex protein having function inhibitory activity against E-cadherin, wherein
(a) all or a part of at least HA1 subcomponent, and/or a part of HA3 subcomponent are/is deleted,
(b) regions in HA2 and HA3 subcomponents that contribute to binding with E-cadherin are present, and
(c) the HA3 subcomponent is derived from Clostridium botulinum type A or type B,
provided that a monovalent complex protein consisting of a full-length HA1 subcomponent dimer, a full-length HA2 subcomponent and a fragment of Pro at position 378 to Asn at position 626 of HA3 subcomponent, each derived from Clostridium botulinum type A, in association is excluded.

[2] The hemagglutinin complex protein of the above-mentioned [1] that is monovalent.

[3] The hemagglutinin complex protein of the above-mentioned [2], wherein the HA3 subcomponent part is
(a) the amino acid sequence shown in SEQ ID NO: 1 or 2, or
(b) the amino acid sequence wherein 1 to several amino acids are substituted, deleted, inserted or added.

[4] The hemagglutinin complex protein of the above-mentioned [2] or [3], wherein the HA2 subcomponent part is
(a) the amino acid sequence shown in any of SEQ ID NO: 3-6, or
(b) the amino acid sequence wherein 1 to several amino acids are substituted, deleted, inserted or added.

[5] The hemagglutinin complex protein of any of the above-mentioned [2] to [4], wherein the HA1 subcomponent is entirely deleted.

[6] The hemagglutinin complex protein of any of the above-mentioned [2] to [5], wherein the HA3 subcomponent and the HA2 subcomponent are linked via a linker.

[7] The hemagglutinin complex protein of the above-mentioned [6], wherein the C-terminal of HA3 subcomponent and the N-terminal of HA2 subcomponent are linked via a linker.

[8] The hemagglutinin complex protein of any of the above-mentioned [2] to [7], wherein the HA2 subcomponent is derived from Clostridium botulinum type C or type D.

[9] The hemagglutinin complex protein of any of the above-mentioned [2] to [8], wherein each of 1 to several hydrophobic amino acid residues which are exposed on the surface of the molecules of the hemagglutinin complex protein and are amino acid residues in the HA2 subcomponent and/or HA3 subcomponent is substituted by a more hydrophilic amino acid.

[10] The hemagglutinin complex protein of the above-mentioned [1] that is trivalent.

[11] The hemagglutinin complex protein of the above-mentioned [10], wherein the HA1 subcomponent is entirely deleted.

[12] The hemagglutinin complex protein of the above-mentioned or [11], wherein the HA2 subcomponent is
(a) the amino acid sequence shown in any of SEQ ID NO: 3-6, or
(b) the amino acid sequence wherein 1 to several amino acids are substituted, deleted, inserted or added.

[13] The hemagglutinin complex protein of any of the above-mentioned [10] to [12], wherein the HA3 subcomponent is (a) a sequence comprising at least a partial sequence of amino acid numbers 19 to 626 in the amino acid sequence shown in SEQ ID NO: 7 or 8, or
(b) the amino acid sequence wherein 1 to several amino acids are substituted, deleted, inserted or added.

[14] The hemagglutinin complex protein of any of the above-mentioned [10] to [13], wherein the HA3 subcomponent and the HA2 subcomponent are linked via a linker.

[15] The hemagglutinin complex protein of the above-mentioned [14], wherein the C-terminal of HA3 subcomponent and the N-terminal of HA2 subcomponent are linked via a linker.

[16] A nucleic acid encoding the hemagglutinin complex protein of any of the above-mentioned [1] to [15].

[17] An expression vector comprising the nucleic acid of the above-mentioned [16].

[18] A host cell comprising the expression vector of the above-mentioned [17] introduced thereinto.

[19] A method for producing a hemagglutinin complex protein comprising culturing the host cell of the above-mentioned [18], collecting a hemagglutinin complex protein or a subcomponent thereof from the obtained culture, in the case of the subcomponent, further contacting the obtained subcomponents with each other and collecting the hemagglutinin complex protein produced thereby.

[20] An E-cadherin function inhibitor comprising the hemagglutinin complex protein of any of the above-mentioned [1] to [15], or a monovalent complex protein consisting of a Clostridium botulinum type A-derived full-length HA1 subcomponent dimer, a full-length HA2 subcomponent and a fragment of Pro at position 378 to Asn at position 626 of HA3 subcomponent in association.

[21] The inhibitor of the above-mentioned [20], wherein the function of E-cadherin is a cell-cell adhesion function.

[22] A method for inhibiting cell-cell adhesion in a cell population comprising bringing the hemagglutinin complex protein of any of the above-mentioned [1] to [15], or a monovalent complex protein consisting of a full-length HA1 subcomponent dimer, a full-length HA2 subcomponent and a fragment of Pro at position 378 to Asn at position 626 of HA3 subcomponent, each derived from Clostridium botulinum type A, in association into contact with the cell population.

[23] The method of the above-mentioned [22], wherein the cell population is a population of pluripotent stem cells.

[24] A cell proliferation promoter comprising the hemagglutinin complex protein of any of the above-mentioned [1] to [15], or a monovalent complex protein consisting of a full-length HA1 subcomponent dimer, a full-length HA2 subcomponent and a fragment of Pro at position 378 to Asn at position 626 of HA3 subcomponent, each derived from Clostridium botulinum type A, in association.

[25] A method for promoting proliferation of a cell comprising culturing the cell in the presence of the hemagglutinin complex protein of any of the above-mentioned [1] to [15], or a monovalent complex protein consisting of a full-length HA1 subcomponent dimer, a full-length HA2 subcomponent and a fragment of Pro at position 378 to Asn at position 626 of HA3 subcomponent, each derived from Clostridium botulinum type A, in association.

Advantageous Effects of Invention

According to the present invention, a miniaturized novel HA complex protein maintaining cadherin function inhibitory activity is provided. Therefore, an HA complex protein for maintaining an undifferentiated state of pluripotent stem cells including iPS cells can be provided conveniently at a low cost, and is extremely useful.

BRIEF DESCRIPTION OF DRAWINGS

FIG. 16A shows the experiment protocol. FIG. 16B is a microscopic photograph showing the cell-cell adhesion inhibitory effect of various concentrations (0.5 to 100 nM) of the FL-HA complex of type B and linked-mini(2+3)/CB-LD/YFDY complex on day 3 from the start of culture (Day3).

on the proliferation of MDCK cells. The number on the horizontal axis shows, from the top, molar concentrations (nM) of both HA complexes, a weight/volume concentration (μg/ml) of the FL-HA complex of type B, and a weight/volume concentration (μg/ml) of the linked-mini(2+3)/CB-LD/YFDY complex.

Figure 18:
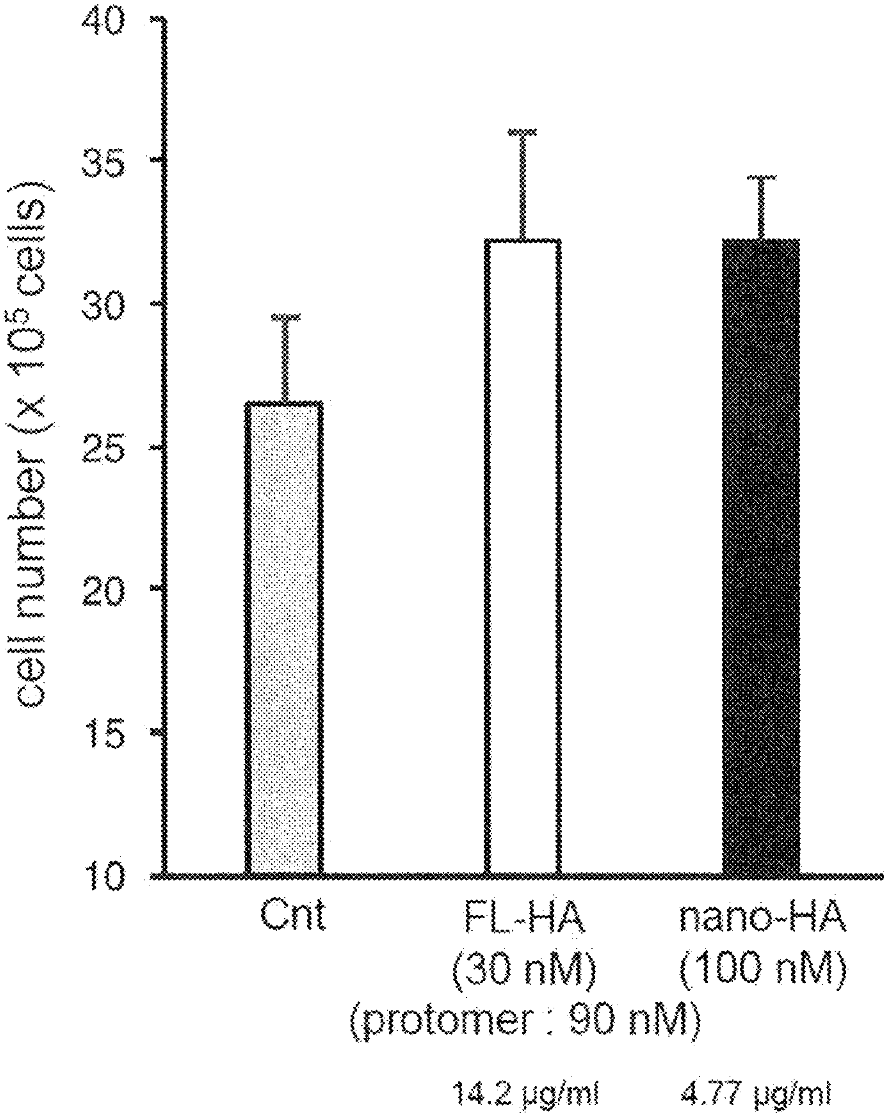

FIG. 18 is a drawing showing the effects of an FL-HA complex of type B (FL-HA; 30 nM (90 nM per single arm (protomer)) and a linked-mini(2+3)/CB-LD/YFDY complex (nano-HA; 100 nM) on the proliferation of MDCK cells. The numerical value in the lower panel of the horizontal axis shows a weight/volume concentration (μg/ml) of each HA complex.

DESCRIPTION OF EMBODIMENTS

The present invention provides a miniaturized HA complex protein having function inhibitory activity against E-cadherin (hereinafter to be also referred to as "the HA complex of the present invention"). The HA complex protein is characterized in that (a) all or a part of at least HA1 subcomponent, and/or a part of HA3 subcomponent are/is deleted, (b) regions in HA2 and HA3 subcomponents that contribute to binding with E-cadherin is present, and (c) the HA3 subcomponent is derived from Clostridium botulinum type A or type B.

The HA complex of the present invention is largely divided into a monovalent type and a trivalent type.

(I) Monovalent HA Complex

In the present specification, the "monovalent" includes a complex consisting of an HA1 subcomponent dimer, an HA2 subcomponent and an HA3 subcomponent as a base (whole type), wherein a part or all of one or more subcomponents is/are deleted. A trivalent HA complex is formed by trimerizing a monovalent HA complex having a triskelion-like conformation, and a whole monovalent HA complex that underwent trimerization is FL-HA (12-mer). It is theoretically impossible to form a triskelion-like trivalent HA complex due to deletion of the N-terminal region of the HA3 subcomponent. Even when two or more monovalent HA complexes are present in association with each other due to some intermolecular interaction, they are included in the monovalent HA complex of the present invention.

The monovalent HA complex of the present invention contains at least regions in HA2 and HA3 subcomponents that contribute to the binding with E-cadherin.

The region in the HA2 subcomponent that contributes to the binding with E-cadherin may be a region containing amino acid residues at positions 83, 86, 104, 109, 131 and 135 which form a hydrogen bond or salt bridge with E-cadherin (see, for example, non-patent document 6). For example, it may be a region containing an amino acid sequence of 80- to 135-positions, preferably 50- to 140-positions, more preferably 2- to 146-positions, of the HA2 subcomponent.

The region in the HA3 subcomponent that contributes to the binding with E-cadherin may be a region containing amino acid residues at positions 501, 503, 505, 506, 534, 535, 582, 586, 607 and 609 which form a hydrogen bond or salt bridge with E-cadherin, and further, a region containing amino acid residues at positions 417, 473 and 508 which are involved in hydrophobic interactions with E-cadherin (see, for example, non-patent document 6), for example, a region containing an amino acid sequence of 400- to 610-positions, preferably 390- to 620-positions, more preferably 380- to 626-positions, of the HA3 subcomponent.

The HA3 subcomponent constituting the monovalent HA complex of the present invention may include an amino acid sequence further on the N-terminal side from the 380-position. When an amino acid sequence further on the C-terminal side than the 380-position is present, function inhibitory activity against E-cadherin can be imparted to the complex. Thus, in one preferable embodiment, from the aspect of miniaturization, the HA3 subcomponent does not contain an amino acid sequence on the N-terminal side from the 380-position. In an embodiment in which each subcomponent is produced separately and then contacted with each other to allow for reconstitution, inclusion of up to the further N-terminal side of the HA3 subcomponent may cause reconstitution into a trivalent form and lower the yield of the monovalent form. Also from this respect, it is desirable not to include an amino acid sequence further on the N-terminal side than the 380-position.

The HA3 subcomponent constituting the monovalent HA complex of the present invention is derived from Clostridium botulinum type A or type B. Examples of the HA3 subcomponent derived from Clostridium botulinum type A include a protein having the amino acid sequence shown in SEQ ID NO: 7 (GenBank: AAM75949.1). Examples of the HA3 subcomponent derived from Clostridium botulinum type B include a protein having the amino acid sequence shown in SEQ ID NO: 8 (GenBank: ACA46977.1). The HA3 subcomponent derived from Clostridium botulinum type A or type B also includes the amino acid sequence shown in SEQ ID NO: 7 or 8 wherein 1 to several (e.g., 2, 3, 4, 5, 6, 7, 8, 9 or 10) amino acids are substituted, deleted, inserted or added. Since the HA3 subcomponent of type A and the HA3 subcomponent of type B have about 98% amino acid identity, examples of the positions at which amino acids are substituted, deleted, inserted or added include positions at which amino acid residues are different between the HA3 of type A and the HA3 of type B. Alternatively, the position of the mutation may be a hydrophobic amino acid residue exposed on the molecular surface of the below-mentioned HA complex protein. When an amino acid residue in the HA3 subcomponent is replaced with another amino acid, it is desirably replaced with a similar amino acid. The "similar amino acid" means an amino acid similar in physicochemical properties and, for example, amino acids classified in the same group such as aromatic amino acids (Phe, Trp, Tyr), aliphatic amino acids (Ala, Leu, Ile, Val), polar amino acids (Gln, Asn), basic amino acids (Lys, Arg, His), acidic amino acids (Glu, Asp), amino acids having hydroxyl group (Ser, Thr), amino acids with small side chain (Gly, Ala, Ser, Thr, Met) and the like can be mentioned. Substitution with such similar amino acids is expected to prevent changes in the phenotype of the protein (i.e., conservative amino acid substitution). Specific examples of conservative amino acid substitution are well known in the art and described in various literatures (e.g., Bowie et al., Science, 247:1306-1310 (1990)).

Therefore, the HA3 subcomponent constituting the monovalent HA complex of the present invention may include, for example, a partial amino acid sequence of the 400- to 610-position, preferably 390- to 620-position, more preferably 380- to 626-position, of the amino acid sequence shown in SEQ ID NO: 7 or 8, or the partial amino acid sequence wherein 1 to several amino acids are substituted, deleted, inserted or added.

In one embodiment, the monovalent HA complex of the present invention may contain the HA2 subcomponent and the HA3 subcomponent, and further, a HA1 subcomponent. The HA1 subcomponent may be derived from any of Clostridium botulinum type A to type D, desirably derived from Clostridium botulinum type A or type B, more desirably derived from Clostridium botulinum type B. Examples of the HA1 subcomponent derived from Clostridium botulinum type A include a protein having the amino acid sequence shown in SEQ ID NO: 9 (GenBank: AAM75951.1). Examples of the HA1 subcomponent derived from Clostridium botulinum type B include a protein having the amino acid sequence shown in SEQ ID NO: 10 (GenBank: ACA46991.1). Examples of the HA1 subcomponent derived from Clostridium botulinum type C include a protein having the amino acid sequence shown in SEQ ID NO: 11 (NCBI reference Sequence: YP 398514.1). Examples of the HA1 subcomponent derived from Clostridium botulinum type D include a protein having the amino acid sequence shown in SEQ ID NO: 12 (GenBank: EES90382.1). The HA1 subcomponent derived from any of Clostridium botulinum type A to type D also includes the amino acid sequence shown in any of SEQ ID NO: 9-12 wherein 1 to several (e.g., 2, 3, 4, 5, 6, 7, 8, 9 or 10) amino acids are substituted, deleted, inserted or added. While the substitution, deletion, insertion and addition of the amino acids are basically the same as those in the aforementioned HA3 subcomponent, since the HA1 subcomponent may be derived from Clostridium botulinum type C or type D, the positional freedom of mutations may be higher than that of the HA3 subcomponent. That is, the HA1 subcomponent of type A and the HA1 subcomponent of type B have about 84% amino acid identity, the HA1 subcomponent of type B and the HA1 subcomponent of type C or type D respectively have about 35%, about 40% amino acid identities, and 568, 58% amino acid identities at most even when similar amino acids are included. Thus, for example, there are more positions where amino acid residues are different between HA2 of type A or type B and HA2 of type C or type D, as the positions where amino acids are substituted, deleted, inserted or added. When an amino acid residue in the HAL subcomponent is substituted by another amino acid, it is desirable to substitute with a similar amino acid. Examples of the "similar amino acid" include those similar to the above. When an amino acid residue in the HA1 subcomponent is deleted, for example, 1 to several (e.g., 2, 3, 4, 5, 6, 7, 8, 9 or 10) amino acids on the N-terminal may be deleted.

The HA1 subcomponent may contain the full length thereof, or a part thereof alone. When a part thereof alone is contained, it is desirable to contain at least a region that contributes to the interactions with E-cadherin. The monovalent HA complex may contain the HA1 subcomponent as a dimer or a monomer.

In one preferable embodiment, the monovalent HA complex of the present invention contains full-length HA1 subcomponent in a dimer. A monovalent complex protein containing a full-length HA1 subcomponent dimer, a full-length HA2 subcomponent, and a fragment of Pro at position 378 to Asn at position 626 of HA3 subcomponent, each derived from Clostridium botulinum type A, in association (mini-HA complex of Jin et al.) has been conventionally reported to bind with E-cadherin but have no barrier disruption activity. However, the present inventors have found that the mini-HA complex has cadherin function inhibitory activity same as that of whole HA 12-mer (FL-HA).

In a preferable embodiment, the monovalent HA complex of the present invention is a complex protein wherein the HA3 subcomponent part is (a) the amino acid sequence shown in SEQ ID NO: 1 or 2, or
(b) the amino acid sequence wherein 1 to several amino acids are substituted, deleted, inserted or added.

The amino acid sequences of SEQ ID NO: 1 and 2 respectively correspond to the amino acid sequence at positions 380 to 626 of the amino acid sequences of SEQ ID NO: 7 and 8. The substitution, deletion, insertion and addition of the amino acids are basically the same as those in the above.

In another preferable embodiment, the monovalent HA complex of the present invention is a complex protein wherein the HA2 subcomponent part is (a) the amino acid sequence shown in any of SEQ ID NO: 3-6, or
(b) the amino acid sequence wherein 1 to several amino acids are substituted, deleted, inserted or added.

The amino acid sequences of SEQ ID NO: 3-6 respectively correspond to the full-length (positions 1 to 146) amino acid sequence (GenBank: AAM75950.1, GenBank: BAE48260.1, NCBI: YP_398513.1 and GenBank: EES90370.1, respectively) of the HA2 subcomponent derived from Clostridium botulinum type A-type D. The substitution, deletion, insertion and addition of the amino acids are basically the same as those in the aforementioned HA3 subcomponent. Since the HA2 subcomponent may be derived from Clostridium botulinum type C or type D, the positional freedom of mutations may be higher than that of the HA3 subcomponent. That is, the HA2 subcomponent of type A and the HA2 subcomponent of type B have about 98% amino acid identity, the HA2 subcomponent of type B and the HA2 subcomponent of type C or type D have 64% amino acid identity, and 79% amino acid identity at most even when similar amino acids are included (see FIG. 12). Thus, for example, there are more positions where amino acid residues are different between HA2 of type A or type B and HA2 of type C or type D, as the positions where amino acids are substituted, deleted, inserted or added.

In the monovalent HA complex of the present invention, the respective HA subcomponents may be expressed as separate proteins and contacted with each other to allow for reconstitution, or may be expressed as a fusion protein via a linker. In the latter case, the production step can be simplified since purification, reconstitution or further purification of each subcomponent is not necessary.

In another preferable embodiment, HA1 subcomponent is entirely deleted from the monovalent HA complex of the present invention. By deleting whole HA1 subcomponent, the molecular weight of the monovalent HA complex can be reduced to not more than half (about 50 kDa). In the embodiment including expression of the HA2 subcomponent and the HA3 subcomponent as separate proteins, followed by reconstitution, an HA2 subcomponent derived from Clostridium botulinum type C or type D needs to be used. This is because function inhibitory activity against E-cadherin may disappear from the monovalent HA complex obtained using an HA2 subcomponent of type A or type B.

Therefore, in one preferable embodiment, the monovalent HA complex of the present invention contains an HA2 subcomponent derived from Clostridium botulinum type C.

In another preferable embodiment, the monovalent HA complex of the present invention may be provided as a fusion protein in which an HA3 subcomponent and an HA2 subcomponent are linked via a linker. When provided as a fusion protein, function inhibitory activity against E-cadherin can be imparted to an HA complex even by using an HA2 subcomponent derived from Clostridium botulinum type A or type B. When an HA2 subcomponent derived from Clostridium botulinum type C or type D is used, the transient cadherin function inhibitory activity can be changed to that in a sustained manner. By expressing as a fusion protein, mixing of contaminants and/or decomposed products can be suppressed, HA complex can be purified at high purity (see FIG. 11), and the yield is remarkably improved, as in the case of separate expression of respective subcomponents, followed by reconstitution.

Figure 13:
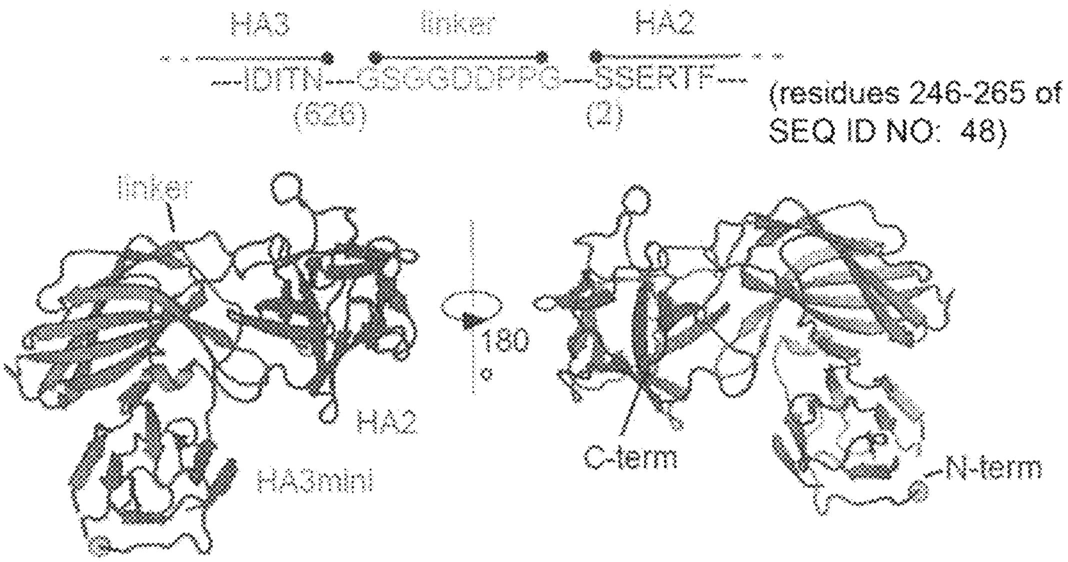
FIG. 13 is a schematic drawing showing the conformation of a linked-mini(2+3) complex. The linker sequence is the sequence of SEQ ID NO: 13.

The linker is not particularly limited as long as it is a peptide linker. In consideration of the conformation of the HA2 subcomponent and the HA3 subcomponent (see FIG. 13), when the C-terminal of the HA3 subcomponent and the N-terminal of the HA2 subcomponent are linked via a linker, a linker composed of any amino acid sequence consisting of 6-12 amino acids, preferably 8-10 amino acids, can be used. Examples thereof include, but are not limited to, GSGGDDPPG (SEQ ID NO: 13).

On the other hand, when the C-terminal of the HA2 subcomponent and the N-terminal of the HA3 subcomponent are linked via a linker, since the both terminals are distant in the conformation of the HA complex, a longer linker is desirably used. It is more preferable to connect the C-terminal of the HA3 subcomponent and the N-terminal of the HA2 subcomponent with a linker, in view of disadvantages such as easy cleavage of the linker by protease or peptidase.

Figure 14:
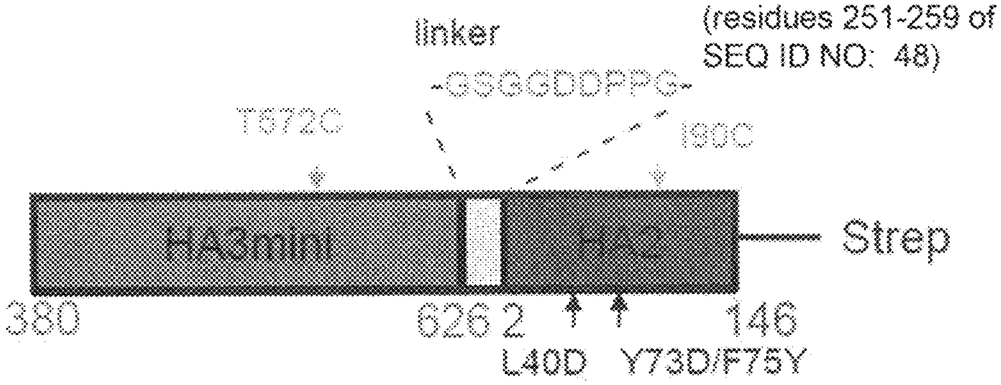
FIG. 14 is a schematic drawing showing introduction of various mutations into a linked-mini(2+3)/CB complex. The linker sequence is the sequence of SEQ ID NO: 13.
Figure 15:
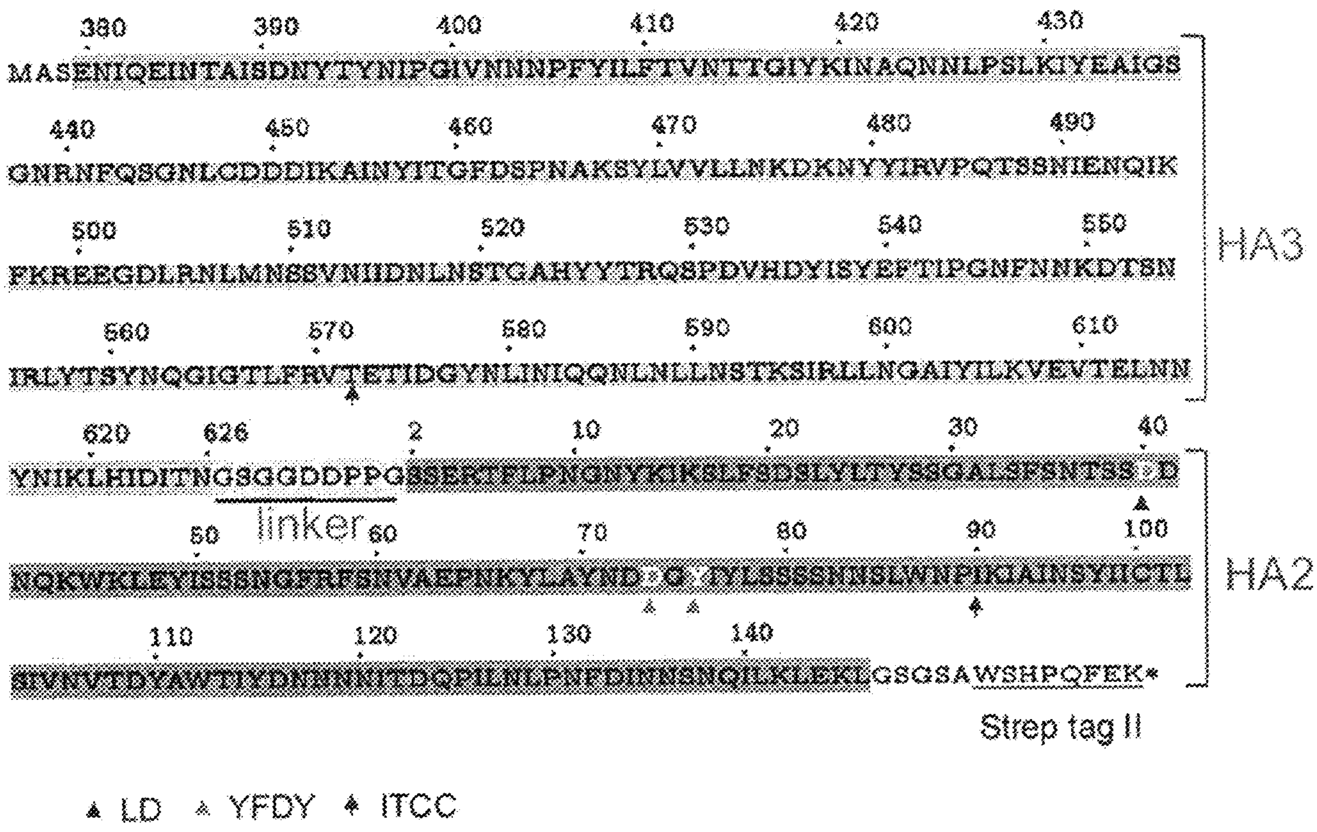
FIG. 15 is a drawing showing the amino acid sequence of a linked-mini(2+3)/CB-LD/YFDY complex (SEQ ID NO: 50).

In yet another preferable embodiment of the present invention, the monovalent HA complex of the present invention can further improve barrier disruption activity by substituting 1 to several hydrophobic amino acid residues exposed on the molecular surface thereof with more hydrophilic amino acids. Examples of the hydrophobicity amino acid when the HA complex is mini-HA(2+3)/CB include F7, F19, L23, L35, L40, I50, V61, A62, Y70, Y73, F75, Y77, L86, I90, I94, L102, I104, V105, V107, Y110, Y115, I121, L127, L129, F132, I134, and L146 in the HA2 subcomponent, and I383, Y393, I397, F406, Y407, L409, I417, L426, I435, G436, I437, Y457, I458, A466, L473, Y481, I491, M508, I514, Y525, V533, Y558, Y561, I565, F569, I575, I581, I583, L590, I596, L599, I603, L613, Y616 and the like in the HA3 subcomponent. Preferable examples thereof include, but are not limited to, substitution of the Leu residue at the 40-position of HA2 with Asp, the Tyr residue at the 73-position with Asp, the Phe residue at the 75-position with Tyr and the like (FIGS. 14 and 15).

In another embodiment of the present invention, a cysteine residue can be introduced into each subcomponent. For example, the Thr residue at the 572-position of the HA3 subcomponent and/or the Ile residue at the 90-position of the HA2 subcomponent can be respectively substituted with Cys (linked-mini(2+3)-YFDY/ITCC, FIGS. 14 and 15). By the mutation, it is possible to change the sustained barrier disruption activity achieved by linking the HA2 subcomponent and the HA3 subcomponent with a linker to transient activity.

(II) Trivalent HA Complex

The present invention also provides the trivalent HA complex protein. The trivalent HA complex does not prevent deletion of a part of the HA3 subcomponent, but it needs to contain a region that contributes to binding with E-cadherin and a region necessary for taking a triskelion-like conformation. The region that contributes to binding with E-cadherin is the same as that in the case of the aforementioned monovalent form. To be reconstituted as a trivalent form, the region needs to include the amino acid sequence on the N-terminal side of the HA3 subcomponent. Therefore, in a preferable embodiment, the trivalent HA complex may contain the full length HA3 subcomponent.

The HA2 subcomponent constituting the trivalent HA complex of the present invention may be a fragment as long as it contains a region that contributes to binding with E-cadherin in the subcomponent. The region that contributes to binding with E-cadherin region is the same as that in the aforementioned monovalent HA complex.

In a preferable embodiment, HA1 subcomponent is entirely deleted from the trivalent HA complex of the present invention. By deleting whole HA1 subcomponent, the molecular weight of the trivalent HA complex can be reduced to close to a half (about 270 kDa).

Regardless of whether the HA complex of the present invention is a monovalent form or a trivalent form, it may have a tag on the terminal to facilitate purification or when it is used for, for example, maintaining undifferentiated pluripotent stem cells, to ensure rapid removal after achieving the purpose. Examples of the tag include, but are not limited to, FLAG tag, His tag, Strep tag and the like. The tag may be attached to the N-terminal of each HA subcomponent or may be added to the C-terminal. In the trivalent HA complex of the present invention, addition of a tag to the N-terminal side of HA3 may lower the cadherin function inhibitory activity, and therefore, a tag is preferably added to the C-terminal side of HA3.

In a preferable embodiment, the trivalent HA complex of the present invention is a complex protein wherein the HA2 subcomponent is (a) the amino acid sequence shown in any of SEQ ID NO: 3-6, or (b) the amino acid sequence wherein 1 to several amino acids are substituted, deleted, inserted or added.

As mentioned above, the amino acid sequences of SEQ ID NO: 3-6 respectively correspond to the full-length (positions 1 to 146) amino acid sequence of the HA2 subcomponent of type A to type D. The substitution, deletion, insertion and addition of the amino acids are basically the same as those in the above.

In another preferable embodiment, the trivalent HA complex of the present invention is a complex protein wherein the HA3 subcomponent part is (a) the amino acid sequence shown in SEQ ID NO: 7 or 8 comprising at least a partial sequence of amino acid numbers 19 to 626 (used in Examples), or (b) the amino acid sequence wherein 1 to several amino acids are substituted, deleted, inserted or added.

The amino acid sequences of SEQ ID NO: 7 and 8 respectively correspond to the full-length amino acid sequences of the HA3 subcomponent of type A and type B. The substitution, deletion, insertion and addition of the amino acids are the same as those in the HA3 subcomponent in the aforementioned monovalent HA complex.

In the trivalent HA complex of the present invention, an HA3 subcomponent and an HA2 subcomponent may also be linked via a linker, as in the aforementioned monovalent HA complex. Examples of the linker include those similar to the above. In addition, the C-terminal of the HA3 subcomponent and the N-terminal of the HA2 subcomponent are preferably linked via a linker, as in the monovalent HA complex.

(III) Production of the HA Complex Protein of the Present Invention

The HA complex protein of the present invention can be produced by introducing an expression vector containing a DNA encoding each subcomponent or a fusion protein thereof into a host cell, culturing same, collecting the subcomponent or fusion protein from the obtained culture, in the case of the subcomponent, further contacting the obtained subcomponents with each other and collecting the HA complex protein produced thereby.

The DNA encoding each subcomponent can be cloned by, for example, synthesizing based on the cDNA sequence information thereof an oligo DNA primer covering the region encoding the desired portion of the protein, and amplifying by a (RT-)PCR method using, as a template, genomic DNA or mRNA fraction prepared from Clostridium botulinum that produces the protein.

The cloned DNA may be ligated as it is or may be digested with a restriction enzyme on demand or added with an appropriate linker and ligated with a DNA encoding other subcomponents, whereby a DNA encoding a fusion protein can be prepared.

An expression vector containing a DNA encoding each subcomponent or a fusion protein thereof can be produced, for example, by ligating the DNA at the downstream of a promoter in a suitable expression vector.

As the expression vector, plasmid derived from *Escherichia coli* (e.g., pBR322, pBR325, pUC12, pUC13); plasmid derived from *Bacillus subtilis* (e.g., pUB110, pTP5, pC194); plasmid derived from yeast (e.g., pSH19, pSH15); insect cell expressing plasmid (e.g., pFast-Bac); animal cell expressing plasmid (e.g., pA1-11, pXT1, pRc/CMV, pRc/RSV, pcDNAI/Neo); bacteriophage such as λphage and the like; insect virus vector such as baculovirus and the like (e.g., BmNPV, AcNPV); animal virus vector such as retrovirus, vaccinia virus, adenovirus and the like, and the like are used.

The promoter may be any as long as it is an appropriate promoter for the host used for gene expression. For example, when the host is an animal cell, SRα promoter, SV40 promoter, LTR promoter, CMV (cytomegalovirus) promoter, RSV (Rous sarcoma virus) promoter, MoMuLV (Moloney murine leukemia virus) LTR, HSV-TK (herpes simplex virus thymidine kinase) promoter and the like are used. Among these, CMV promoter, SRα promoter and the like are preferable. When the host is *Escherichia coli*, trp promoter, lac promoter, recA promoter, $\lambda P_L$ promoter, lpp promoter, T7 promoter and the like are preferable. When the host is genus *Bacillus*, SPO1 promoter, SPO2 promoter, penP promoter and the like are preferable. When the host is yeast, Gal1/10 promoter, PHO5 promoter, PGK promoter, GAP promoter, ADH promoter and the like are preferable.

As the expression vector, one containing, when desired, enhancer, splicing signal, terminator, poly A addition signal, selection marker of drug resistance gene, complementing auxotrophic complementary gene and the like can be used besides those mentioned above.

RNA encoding each subcomponent or a fusion protein thereof of the HA complex protein of the present invention can be prepared, for example, by transcription into mRNA in an in vitro transcription system known per se and using a vector encoding the DNA encoding the above-mentioned each subcomponent or a fusion protein thereof as a template.

An expression vector containing a DNA encoding each subcomponent or a fusion protein thereof is introduced into a host cell, and the host cell is cultured, whereby the subcomponent or fusion protein can be expressed in the host cell.

As the host, for example, *Escherichia coli*, genus *Bacillus*, yeast, insect cell, insect, animal cell, and the like are used. As the *Escherichia coli, Escherichia coli* K12 DH1 [Proc. Natl. Acad. Sci. USA, 60, 160 (1968)], *Escherichia coli* JM103 [Nucleic Acids Research, 9, 309 (1981)], *Escherichia coli* JA221 [Journal of Molecular Biology, 120, 517 (1978)], *Escherichia coli* HB101 [Journal of Molecular Biology, 41, 459 (1969)], *Escherichia coli* C600 [Genetics, 39, 440 (1954)] and the like are used. As the genus *Bacillus, Bacillus subtilis* MI114 [Gene, 24, 255 (1983)], *Bacillus subtilis* 207-21 [Journal of Biochemistry, 95, 87 (1984)] and the like are used. As the yeast, *Saccharomyces cerevisiae AH*22, AH22R$^-$, NA87-11A, DKD-5D, 20B-12, *Schizosaccharomyces pombe* NCYC1913, NCYC2036, *Pichia pastoris=Komagataella phaffii* KM71 and the like are used.

Introduction of an expression vector can be performed by a known method (e.g., lysozyme method, competent method, PEG method, $CaCl_2$ coprecipitation method, electroporation method, the microinjection method, the particle gun method, lipofection method, Agrobacterium method and the like) according to the kind of the host. *Escherichia coli* can be transformed according to the methods described in, for example, Proc. Natl. Acad. Sci. USA, 69, 2110 (1972), Gene, 17., 107 (1982) and the like. The genus *Bacillus* can be introduced into a vector according to the method described in, for example, Molecular & General Genetics, 168, 111 (1979) and the like. The yeast can be introduced into a vector according to the method described in, for example, Methods in Enzymology, 194, 182-187 (1991), Proc. Natl. Acad. Sci. USA, 75, 1929 (1978) and the like.

The cells having a vector introduced therein can be cultured by a known method according to the kind of the host. For example, when *Escherichia coli* or genus *Bacillus* is cultured, the medium is preferably a liquid medium. The medium preferably contains carbon source, nitrogen source, inorganic substance and the like necessary for the growth of the transformant. Examples of the carbon source include glucose, dextrin, soluble starch, sucrose and the like; examples of the nitrogen source include inorganic or organic substances such as ammonium salts, nitrate salts, corn steep liquor, peptone, casein, meat extract, soybean cake, potato extract and the like; and examples of the inorganic substance include calcium chloride, sodium dihydrogen phosphate, magnesium chloride and the like. In addition, the medium may contain yeast extract, vitamins, growth promoting factor and the like. The pH of the medium is preferably about 5-about 8.

When *Escherichia coli* is cultured, the medium is preferably M9 medium containing glucose and casamino acid [Journal of Experiments in Molecular Genetics, 431-433, Cold Spring Harbor Laboratory, New York 1972]. Where necessary, an agent such as 3β-indolylacrylic acid may be added to the medium to ensure efficient action of the promoter. *Escherichia coli* is cultured generally at about 15-about 43° C. Where necessary, aeration and stirring may be performed.

The genus *Bacillus* is cultured generally at about 30-about 40° C. Where necessary, aeration and stirring may be performed.

When the yeast is cultured, the medium is preferably a Burkholder minimum medium [Proc. Natl. Acad. Sci. USA, 77, 4505 (1980)], SD medium containing 0.5% casamino acid [Proc. Natl. Acad. Sci. USA, 81, 5330 (1984)] or the like. The pH of the medium is preferably about 5-about 8. The culture is performed generally at about 20° C.-about 35° C. Where necessary, aeration and stirring may be performed.

As described above, each subcomponent or a fusion protein thereof can be expressed in a host cell. These proteins can be recovered and purified easily by using an antibody against them, or when a tag is added to the protein, using a substance specific to the tag, for example, by immobilizing them on a carrier, and bringing the obtained culture of the host cell into contact with the carrier. In addition, these proteins may be purified by appropriately combining separation and purification methods of any other proteins known per se.

When respective subcomponents are expressed as separate proteins, the respective subcomponents are purified by the above-mentioned method, mixed according to a conventional method, and incubated under appropriate conditions, whereby they can be reconstituted into the HA complex protein of the present invention.

(IV) Use of the HA Complex Protein of the Present Invention

In the HA complex protein of the present invention, the function of E-cadherin, preferably intercellular barrier function inhibitory activity (i.e., barrier disruption activity) is maintained and the molecular size is miniaturized. Thus, the HA complex protein is easily produced, is superior in handling, and can be used more advantageously in the use of conventionally-known HA complex protein than the conventional products.

Therefore, the present invention also provides an E-cadherin function inhibitor containing the HA complex protein of the present invention (hereinafter to be also referred to as “the inhibitor of the present invention”). Particularly, the inhibitor of the present invention is useful in inhibiting the cell-cell adhesion function of E-cadherin and may be used as, for example, a dissociation agent for an adhered cell population.

In a particularly preferable embodiment, the inhibitor of the present invention can be used in maintaining an undifferentiated state of pluripotent stem cells because it efficiently removes deviated cells that develop accidentally during the process of maintenance and expansion of pluripotent cells and/or suppresses the development. HA complex proteins added to the medium are absorbed into cells by endocytosis and the like, decomposed and removed. The HA complex protein of the present invention having a miniaturized molecular size is considered to be more efficiently absorbed and removed by cells than conventional products. In addition, suspension culture of iPS cells in the presence of the HA complex protein of the present invention permits efficient division of iPS cell clump, and efficient amplification of a large amount of iPS cells. The detail of these methods is described in the above-mentioned patent documents 1 and 2.

When the inhibitor of the present invention is used as a dissociation agent for an adhered cell population, it can be performed by adding the inhibitor to a medium for the cell population. The amount of the inhibitor of the present invention to be added to the medium is not particularly limited as long as the cell-cell adhesion in the target cell population is inhibited and the adhered cells can be dissociated. For example, when linked-mini(2+3)/CB-LD/YFDY is added as an HA complex protein to a maintenance culture system of iPS cells, for example, it can be added to the medium at a concentration of not less than 25 nM, preferably not less than 50 nM, more preferably not less than 100 nM. The upper limit of the addition concentration is not particularly set as long as it does not adversely influence the cell survival. It is, for example, not more than 1 μM, preferably not more than 500 nM. The period of addition of the inhibitor of the present invention to the medium is not particularly limited as long as the cell-cell adhesion in the target cell population is inhibited, the adhered cells can be dissociated, and the cell survival is not adversely influenced. It is, for example, 6-72 hr, preferably 12-48 hr, more preferably 24±6 hr. The cell population can be cultured under culture conditions known per se and suitable for the target cells.

The HA complex protein of the present invention is low toxic, does not show an adverse influence on the cell survival, and rather has a cell proliferation promoting action. Therefore, the present invention also provides a cell proliferation promoter containing the HA complex protein of the present invention (hereinafter to be also referred to as “the proliferation promoter of the present invention”).

The proliferation promoter of the present invention can be used by adding the medicament to a medium for the cell of interest. The amount of the proliferation promoter of the present invention to be added to the medium is not particularly limited as long as it can significantly increases the proliferation of the cell of interest. For example, when linked-mini(2+3)/CB-LD/YFDY is added as an HA complex protein to a culture system of MDCK cells, for example, it can be added to the medium at a concentration of not less than 25 nM, preferably not less than 50 nM, more preferably not less than 100 nM. The upper limit of the addition concentration is not particularly set as long as it does not adversely influence the cell survival. It is, for example, not more than 1 μM, preferably not more than 500 nM. The period of addition of the proliferation promoter of the present invention to the medium is not particularly limited as long as the proliferation of the cell of interest is significantly increased and the cell survival is not adversely influenced. It is, for example, 6-168 hr, preferably 12-120 hr, more preferably 24-96 hr. The cells can be cultured under culture conditions known per se and suitable for the target cells.

The present invention is explained in more detail in the following by referring to Examples; however, the present invention is not limited to the Examples.

Example

Materials and Methods

(1) Production of Plasmid

(I) Alteration of pET52b+ (pET52b-C)

The following primers were inserted into the NcoI-SalI site of pET52b+ [Novagen].

```
C-strep-f (SEQ ID NO: 14):
taccatggctagcgcaagctacggatccggtagtgcatggagccacccgc

agttcgaaaagtaagtcgacgc

C-strep-r (SEQ ID NO: 15):
gcgtcgacttacttttcgaactgcgggtggctccatgcactaccggatcc

gtagcttgcgctagccatggta
```

(II) FL-HA/B (FL-HA of Type B)

His-BHA1-Flag (7-294 a.a).
His-BHA2 (2-146 a.a.)
Strep-BHA3 (19-626 a.a.)

Amplification was performed by the PCR method using genomic DNA of Clostridium botulinum B-okra strain as a template and the following primers.

HA1/B-f (SEQ ID NO: 16):
ctagctagcatccaaaattcattaaatgac

HA1/B-r (SEQ ID NO: 17):
cgggatccttacttgtcgtcatcgtctttgtagtctgggttactcatagt ccatatc HA2/B-f (SEQ ID NO: 18):
ctagctagctcagctgaaagaacttttctac HA2/B-r (SEQ ID NO: 19):
ccgctcgagttatattttttcaagtttgaacatttg HA3/B-f (SEQ ID NO: 20):
gaaaaagggtaccaatatagtgatactattg HA3/B-r (SEQ ID NO: 21):
cgtgtcgacttaattagtaatatctatatgc HA1 was inserted into the NheI-BamHI site of pET28b+ (Novagen), HA2 was inserted into the NheI-XhoI site of pET28b+ (Novagen), and HA3 was inserted into the KpnI-SalI site of pET52b+ (Novagen).

(III) N-FL-HA(2+3)/B (FL(2+3) of B Type with Strep Tag Added to the N-Terminal of HA3)

His-BHA2 (2-146 a.a.)

Strep-BHA3 (19-626 a.a.)

Amplification was performed by the PCR method using genomic DNA of Clostridium botulinum B-okra strain as a template and the following primers.

HA2/B-f (SEQ ID NO: 18):
ctagctagctcagctgaaagaacttttctac

HA2/B-r (SEQ ID NO: 19):
ccgctcgagttatattttttcaagtttgaacatttg

HA3/B-f (SEQ ID NO: 20):
gaaaaagggtaccaatatagtgatactattg

HA3/B-r (SEQ ID NO: 21):
cgtgtcgacttaattagtaatatctatatgc

HA2 was inserted into NheI-XhoI site of pET28b+ (Novagen), and HA3 was inserted into KpnI-SalI site of pET52b+ (Novagen).

(IV) C-FL-HA (2+3)/B (FL(2+3) of B Type with Strep Tag Added to the C-Terminal of HA3)

His-BHA2 (2-146 a.a.)

BHA3-Strep (19-626 a.a.)

Amplification was performed by the PCR method using genomic DNA of Clostridium botulinum B-okra strain as a template and the following primers.

HA2/B-f (SEQ ID NO: 18):
ctagctagctcagctgaaagaacttttctac

HA2/B-r (SEQ ID NO: 19):
ccgctcgagttatattttttcaagtttgaacatttg

HA3/B-f (SEQ ID NO: 22):
gcgctagcaatatagtgatactattgatttagctgatgg

HA3/B-r (SEQ ID NO: 23):
ccggatccattagtaatatctatatgcaattttatattatag

HA2 was inserted into NheI-XhoI site of pET28b+ (Novagen), and HA3 was inserted into NheI-BamHI site of pET52b-C.

(V) Linked-FL-HA (2+3)/B(Linked-FL(2+3) of Type B)

BHA3-linker-BHA2-Strep (19-626 a.a+1-9 a.a.+2-146 a.a.)

Amplification was performed by the PCR method using pET28b-BHA2 and pET52b-BHA3 as templates and the following primers.

HA2/B-f (SEQ ID NO: 24):
ggggtgatgaccctccaggatcagctgaaagaacttttctacctaatg

HA2/B-r (SEQ ID NO: 25):
actaccggatcctatttttcaagtttgaacatttg

HA3/B-f (SEQ ID NO: 26):
taagaaggagatataccatggctagc

HA3/B-r (SEQ ID NO: 27):
gggtcatcacccccacttccattagtaatatctatatgcaattttatatt ata

HA2 and HA3 were inserted into NcoI-BamHI site of pET52b-C by using GeneArt (registered trade mark) Seamless Cloning and Assembly Kit (Invitrogen).

(VI) Mini-HA/B (Mini-HA of Type B)

His-BHA1-FLAG (7-294 a.a).

His-BHA2 (2-146 a.a.).

BHA3mini-Strep (380-626 a.a.)

Amplification was performed by the PCR method using genomic DNA of Clostridium botulinum B-okra strain as a template and the following primers.

HA1/B-f (SEQ ID NO: 16):
ctagctagcatccaaaattcattaaatgac

HA1/B-r (SEQ ID NO: 17):
cgggatccttacttgtcgtcatcgtctttgtagtctgggttactcatagt ccatatc HA2/B-f (SEQ ID NO: 18):
ctagctagctcagctgaaagaacttttctac HA2/B-r (SEQ ID NO: 19):
ccgctcgagttatattttttcaagtttgaacatttg HA3mini/B-f (SEQ ID NO: 28):
gcgctaqcgaaaatatacaagaaataaatactgctatttcag HA3mini/B-r (SEQ ID NO: 23):
ccggatccattagtaatatctatatgcaattttatattatag HA1 was inserted into NheI-BamHI site of pET28b+ (Novagen), HA2 was inserted into NheI-XhoI site of pET28b+ (Novagen), and HA3mini was inserted into NheI-BamHI site of pET52b-C.

(VII) Mini-HA(2+3)/B(Mini(2+3) of Type B)

His-BHA2 (2-146 a.a.)

BHA3mini-Strep (380-626 a.a.)

Amplification was performed by the PCR method using genomic DNA of Clostridium botulinum B-okra strain as a template and the following primers.

```
HA2/B-f (SEQ ID NO: 18):
ctagctagctcagctgaaagaacttttctac

HA2/B-r (SEQ ID NO: 19):
ccgctcgagttatatttttcaagtttgaacatttg

HA3mini/B-f (SEQ ID NO: 28):
gcgctagcgaaaatatacaagaaataaatactgctatttcag

HA3mini/B-r (SEQ ID NO: 23):
ccggatccattagtaatatctatatgcaattttatattatag
```

HA2 was inserted into NheI-XhoI site of pET28b+ (Novagen), and HA3mini was inserted into NheI-BamHI site of pET52b-C.

(VIII) Mini-HA(2+3)/CB(Mini(2+3)/CB)

His-CHA2 (2-146 a.a.)

BHA3mini-Strep (380-626 a.a.)

Amplification was performed by the PCR method using genomic DNAs of Clostridium botulinum C-st strain, B-okra strain as templates and the following primers.

```
HA2/C-f (SEQ ID NO: 29):
ctagctagctcaagtgaaagaaccttttac

HA2/C-r (SEQ ID NO: 30):
acgcgtcgacttaaagtttttctaattttaaaatttg

HA3mini/B-f (SEQ ID NO: 28):
gcgctagcgaaaatatacaagaaataaatactgctatttcag

HA3mini/B-r (SEQ ID NO: 23):
ccggatccattagtaatatctatatgcaattttatattatag
```

HA2 was inserted into NheI-SalI site of pET28b+ (Novagen), and HA3mini was inserted into NheI-BamHI site of pET52b-C.

(IX) Linked-Mini-HA(2+3)/B(Linked-Mini(2+3)/BB)

BHA3mini-linker-BHA2-Strep (380-626 a.a+1-9 a.a.+2-146 a.a.)

Amplification was performed by the PCR method using pET28b-BHA2 and pET52b-BHA3 as templates and the following primers.

```
HA2/B-f (SEQ ID NO: 24):
ggggtgatgaccctccaggatcagctgaaagaacttttctacctaatg

HA2/B-r (SEQ ID NO: 25):
actaccggatcctatttttcaagttgaacatttg

HA3mini/B-f (SEQ ID NO: 26):
taagaaggagatataccatggctagc

HA3mini/B-r (SEQ ID NO: 27):
gggtcatcacccccacttccattagtaatatctatatgcaattttatatt

ata
```

HA2 and HA3mini were inserted into NcoI-BamHI site of pET52b-C by using GeneArt (registered trade mark) Seamless Cloning and Assembly Kit (Invitrogen).

(X) Linked-Mini-HA(2+3)/CB(Linked-Mini(2+3)/CB)

BHA3mini-linker-CHA2-Strep (380-626 a.a+1-9 a.a.+2-146 a.a.)

Amplification was performed by the PCR method using pET28b-CHA2 and pET52b-BHA3 as templates and the following primers.

```
HA2/C-f (SEQ ID NO: 31):
ggggtgatgaccctccaggatcaagtgaaagaaccttttacctaatg

HA2/C-r (SEQ ID NO: 32):
actaccggatccaagtttttctaattttaaaatttgattag

HA3mini/B-f (SEQ ID NO: 26):
taagaaggagatataccatggctagc

HA3mini/B-r (SEQ ID NO: 27):
gggtcatcacccccacttcc attagtaatatctatatgcaattttatat

tata
```

HA2 and HA3mini were inserted into NcoI-BamHI site of pET52b-C by using GeneArt (registered trade mark) Seamless Cloning and Assembly Kit (Invitrogen).

(XI) Linked-Mini-HA(2+3)/CB-YFDY (Linked-Mini(2+3)/CB-YFDY)

HA2-Y73D-F75Y

Mutation was introduced by the site-directed mutagenesis method using pET52b-C-linked-mini-HA(2+3)/CB as a template and the following primers.

```
Y73D/F75Y-f (SEQ ID NO: 33):
atgatgatggttatatctatttaagttcatcatctaataatag

Y73D/F75Y-r (SEQ ID NO: 34):
agatataaccatcatcattataagctaaatatttattagg
```

(XII) Linked-Mini-HA(2+3)/CB-IC(Linked-Mini(2+3)/CB-IC)

HA2-Y73D-F75Y-190C

Mutation was introduced by the site-directed mutagenesis method using pET52b-C-linked-mini-HA(2+3)/CB-YFDY as a template and the following primers.

```
I90C-f (SEQ ID NO: 35):
aatccttgtaaaattgctataaattcttatattatatg

I90C-r (SEQ ID NO: 36):
aattttacaaggattccataaactattattag
```

(XIII) Linked-Mini-HA(2+3)/CB-ITCC(Linked-Mini(2+3)/CB-ITCC)

HA2-Y73D-F75Y-190C, HA3-T572C

Mutation was introduced by the site-directed mutagenesis method using pET52b-C-linked-mini-HA(2+3)/CB-YFDY-IC as a template and the following primers.

```
T572C-f (SEQ ID NO: 37):
agagtctgtgaaactattgacggctataattt

T572C-r (SEQ ID NO: 38):
agtttcacagactctaaataaagtacctattc
```

(XIV) Linked-Mini-HA(2+3)/CB-YFDY-LD (Linked-Mini(2+3)/CB-LD/YFDY)

HA2-L40D-Y73D-F75Y

Mutation was introduced by the site-directed mutagenesis method using pET52b-C-linked-mini-HA(2+3)/CB-YFDY as a template and the following primers.

```
L40D-f (SEQ ID NO: 39):
tcttctgatgataatcaaaaatggaagttag

L40D-r (SEQ ID NO: 40):
attatcatcagaagatgtatttgaaaatgataatg
```

(2) Protein Expression

The plasmids produced above were transformed into Rosetta2 (DE3) [Novagen]. Protein expression was induced using Overnight Express Autoinduction System 1 [Novagen]. After induction of expression of each plasmid as follows, *Escherichia coli* was collected by centrifugation and preserved at −80° C. until use.

pET28b-BHA1 . . . 18° C., 48 hr
pET28b-BHA2 . . . 18° C., 48 hr
pET28b-CHA2 . . . 18° C., 48 hr
pET52b-BHA3 . . . 30° C., 36 hr
pET52b-C-BHA3 . . . 30° C., 36 hr
pET52b-C-BHA3mini . . . 30° C., 36 hr
pET52b-C-linked-mini-HA(2+3)/B . . . 30° C., 20 hr
pET52b-C-linked-mini-HA(2+3)/CB . . . 30° C., 20 hr Performed for each variant under the same conditions as for the wild-type.

(3) Protein Purification

Respective proteins were purified using the following.

pET28b-BHA1 . . . His-Trap HP [GE Healthcare]
pET28b-BHA2 . . . His-Trap HP [GE Healthcare]
pET28b-CHA2 . . . His-Trap HP [GE Healthcare]
pET52b-BHA3 . . . Strep-Trap HP [GE Healthcare]
pET52b-C-BHA3 . . . Strep-Trap HP [GE Healthcare]
pET52b-C-BHA3mini . . . Strep-Trap HP [GE Healthcare]
pET52b-C-linked-mini-HA(2+3)/B . . . Strep-Trap HP [GE Healthcare]
pET52b-C-linked-mini-HA(2+3)/CB . . . Strep-Trap HP [GE Healthcare]

In the complexes (II, III, IV, VI, VII, VIII), they were mixed at a molar ratio of (HA1:)HA2:HA3=(4:)4:1, incubated at 37° C. for 3 hr, and purified using Strep-Trap HP [GE Healthcare].

(4) Protein Amino Acid Sequence (Tag(and Vector-Derived Sequence) or Linker Sequence are/is Underlined)

```
>His-BHA1-Flag (SEQ ID NO: 41):
MGSSHHHHHHSSGLVPRGSHMASIQNSLNDKIVTISCKANTDLFFYQVPGNGNVSLFQQTRNY

LERWRIIYDSNKAAYKIKSMNIYNTNLVLTWNAPTHNISAQQDSNADNQYWLLLKDIGNNSFI

IASYKNPNLVLYADTVARNLKLSTLNNSSYIKFIIEDYVISDFKNFTCRISPILAGGKVVQQV

SMTNLAVNLYIWNNDLNQKWTIIYNEEKAAYQFFNKILSNGVLTWIFSDGNTVRVSSSAQNND

AQYWLINPVSDNYDRYTITNLRDKTKVLDLYGGQTADGTTIQVFNSNGGDNQIWTMSNPDYKD

DDDK

>His-BHA2 (SEQ ID NO: 42):
MGSSHHHHHHSSGLVPRGSHMASSAERTFLPNGNYNIKSIFSGSLYLSPVSGSLTESNESSAN

NQKWNVEYMAENRCFKISNVAEPNKYLSYDNEGFISLDSLSNRCYWFPIKIAVNTYIMLSLNK

VNELDYAWDIYDTNENILSQPLLLLPNFDIYNSNQMFKLEKI

>Strep-BHA3 (SEQ ID NO: 43):
MASWSHPQFEKGALEVLFQGPGYQYSDTIDLADGNYVVSRGDGWILSRQNQILGGSVISNGST

GIVGDLRVNDNAIPYYYPTPSFNEEYIKNNIQTVFANFTEANQIPIGFEFSKTAPSNKNLYMY

LQYTYIRYEIIKVLQHEIIERAVLYVPSLGYVKSIEFNPGEKINKDFYFLTNDKCILNEQFLY

KKILETTKNIPTNNIFNSKVSSTQRVLPYSNGLYVINKGDGYIRTNDKDLIGTLLIEAGSSGS

IIQPRLRNTTRPLFTTSNDAKFSQQYTEERLKDAFNVQLFNTSTSLFKFVEEAPSNKNICIKA

YNTYEKYELIDYQNGSIVNKAEYYLPSLGYCEVTNAPSPESEVVKTQVAEDGFIQNGPEEEIV

VGVIDPSENIQEINTAISDNYTYNIPGIVNNNPFYILFTVNTTGIYKINAQNNLPSLKIYEAI

GSGNRNFQSGNLCDDDIKAINYITGFDSPNAKSYLVVLLNKDKNYYIRVPQTSSNIENQIKFK

REEGDLRNLMNSSVNIIDNLNSTGAHYYTRQSPDVHDYISYEFTIPGNFNNKDTSNIRLYTSY

NQGIGTLFRVTETIDGYNLINIQQNLNLLNSTKSIRLLNGAIYILKVEVTELNNYNIKLHIDI

TN
```

-continued

>BHA3-Strep (SEQ ID NO: 44):
MASYSDTIDLADGNYVVSRGDGWILSRQNQILGGSVISNGSTGIVGDLRVNDNAIPYYYPTPS
FNEEYIKNNIQTVFANFTEANQIPIGFEFSKTAPSNKNLYMYLQYTYIRYEIIKVLQHEIIER
AVLYVPSLGYVKSIEFNPGEKINKDFYFLTNDKCILNEQFLYKKILETTKNIPTNNIENSKVS
STQRVLPYSNGLYVINKGDGYIRTNDKDLIGTLLIEAGSSGSIIQPRLRNTTRPLFTTSNDAK
FSQQYTEERLKDAFNVQLFNTSTSLFKFVEEAPSNKNICIKAYNTYEKYELIDYQNGSIVNKA
EYYLPSLGYCEVTNAPSPESEVVKTQVAEDGFIQNGPEEEIVVGVIDPSENIQEINTAISDNY
TYNIPGIVNNNPFYILFTVNTTGIYKINAQNNLPSLKIYEAIGSGNRNFQSGNLCDDDIKAIN
YITGFDSPNAKSYLVVLLNKDKNYYIRVPQTSSNIENQIKFKREEGDLRNLMNSSVNIIDNLN
STGAHYYTRQSPDVHDYISYEFTIPGNFNNKDTSNIRLYTSYNQGIGTLFRVTETIDGYNLIN
IQQNLNLLNSTKSIRLLNGAIYILKVEVTELNNYNIKLHIDITNGSGSAWSHPQFEK >linked-FL(2 + 3)/BB(SEQ ID NO: 45):
MASYSDTIDLADGNYVVSRGDGWILSRQNQILGGSVISNGSTGIVGDLRVNDNAIPYYYPTPS
FNEEYIKNNIQTVFANFTEANQIPIGFEFSKTAPSNKNLYMYLQYTYIRYEIIKVLQHEIIER
AVLYVPSLGYVKSIEFNPGEKINKDFYFLTNDKCILNEQFLYKKILETTKNIPTNNIFNSKVS
STQRVLPYSNGLYVINKGDGYIRTNDKDLIGTLLIEAGSSGSIIQPRLRNTTRPLFTTSNDAK
FSQQYTEERLKDAFNVQLFNTSTSLFKFVEEAPSNKNICIKAYNTYEKYELIDYQNGSIVNKA
EYYLPSLGYCEVTNAPSPESEVVKTQVAEDGFIQNGPEEEIVVGVIDPSENIQEINTAISDNY
TYNIPGIVNNNPFYILFTVNTTGIYKINAQNNLPSLKIYBAIGSGNRNFQSGNLCDDDIKAIN
YITGFDSPNAKSYLVVLLNKDKNYYIRVPQTSSNIENQIKFKREEGDLRNLMNSSVNIIDNLN
STGAHYYTRQSPDVHDYISYEFTIPGNFNNKDTSNIRLYTSYNQGIGTLFRVTETIDGYNLIN
IQQNLNLLNSTKSIRLLNGAIYILKVEVTELNNYNIKLHIDITNGSGGDDPPGSAERTFLPNG
NYNIKSIFSGSLYLSPVSGSLTFSNESSANNQKWNVEYMAENRCFKISNVAEPNKYLSYDNPG
FISLDSLSNRCYWFPIKIAVNTYIMLSLNKVNELDYAWDIYDTNENILSQPLLLLPNFDIYNS
NQMFKLEKIGSGSAWSHPQFEK >BHA3mini-Strep (SEQ ID NO: 46):
MASENIQEINTAISDNYTYNIPGIVNNNPFYILFTVNTTGIYKINAQNNLPSLKIYEAIGSGN
RNFQSGNLCDDDIKAINYITGFDSPNAKSYLVVLLNKDKNYYIRVPQTSSNIENQIKFKREEG
DLRNLMNSSVNIIDNLNSTGAHYYTRQSPDVHDYISYEFTIPGNFNNKDTSNIRLYTSYNQGI
GTLFRVTETIDGYNLINIQQNLNLLNSTKSIRLLNGAIYILKVEVTELNNYNIKLHIDITNGS
GSAWSHPQFEK >linked-mini(2 + 3)/BB (SEQ ID NO: 47):
MASENIQEINTAISDNYTYNIPGIVNNNPFYILFTVNTTGIYKINAQNNLPSLKIYEAIGSGN
RNFQSGNLCDDDIKAINYITGFDSPNAKSYLVVLLNKDKNYYIRVPQTSSNIENQIKFKREEG
DLRNLMNSSVNIIDNLNSTGAHYYTRQSPDVHDYISYEFTIPGNFNNKDTSNIRLYTSYNQGI
GTLFRVTETIDGYNLINIQQNLNLINSTKSIRLLNGAIYILKVEVTELNNYNIKLHIDITNGS
GGDDPPGSAERTFLPNGNYNIKSIFSGSLYLSPVSGSLTFSNESSANNQKWNVEYMAENRCFK
ISNVAEPNKYLSYDNFGFISLDSLSNRCYWFPIKIAVNTYIMLSLNKVNELDYAWDIYDTNEN
ILSQPLLLLPNFDIYNSNQMFKLEKIGSGSAWSHPQFEK >linked-mini (2 + 3)/CB (SEQ ID NO: 48):
MASENIQEINTAISDNYTYNIPGIVNNNPFYILFTVNTTGIYKINAQNNLPSLKIYEAIGSGN
RNFQSGNLCDDDIKAINYITGFDSPNAKSYLVVLLNKDKNYYIRVPQTSSNIENQIKFKREEG
DLRNLMNSSVNIIDNLNSTGAHYYTRQSPDVHDYISYEFTIPGNFNNICTSNIRLYTSYNQGI -continued

GTLFRVTETIDGYNLINIQQNLNLLNSTKSIRLLNGAIYILKVEVTELNNYNIKLHIDITNGS

GGDDPPGSSERTFLPNGNYKIKSLFSDSLYLTYSSGALSFSNTSSLDNQKWKLEYISSSNGFR

FSNVAEPNKYLAYNDYGFIYLSSSSNNSLWNPIKIAINSYIICTLSIVNVTDYAWTIYDNNNN

ITDQPILNLPNFDINNSNQILKLEKLGSGSAWSHPQFEK

>linked-mini (2 + 3)/CB-YFDY (SEQ ID NO: 49):
MASENIQEINTAISDNYTYNIPGIVNNNPFYILFTVNTTGIYKINAQNNLPSLKIYEAIGSGN

RNFQSGNLCDDDIKAINYITGFDSPNAKSYLVVLLNKDKNYYIRVPQTSSNIENQIKFKREEG

DLRNLMNSSVNIIDNLNSTGAHYYTRQSPDVHDYISYEFTIPGNFNNKDTSNIRLYTSYNQGI

GTLFRVTETIDGYNLINIQQNLNLLNSTKSIRLLNGAIYILKVEVTELNNYNIKLHIDITNGS

GGDDPPGSSERTFLPNGNYKIKSLFSDSLYLTYSSGALSFSNTSSLDNQKWKLEYISSSNGFR

FSNVAEPNKYLAYNDDGYIYLSSSSNNSLWNPIKIAINSYIICTLSIVNVTDYAWTIYDNNNN

ITDQPILNLPNFDINNSNQILKLEKLGSGSAWSHPQFEK

>linked-mini (2 + 3)/CB-LD/YFDY (SEQ ID NO: 50):
MASENIQEINTAISDNYTYNIPGIVNNNPFYILFTVNTTGIYKINAQNNLPSLKIYEAIGSGN

RNFQSGNLCDDDIKAINYITGFDSPNAKSYLVVLLNKDKNYYIRVPQTSSNIENQIKFKREEG

DLRNLMNSSVNIIDNLNSTGAHYYTRQSPDVHDYISYEFTIPGNFNNKDTSNIRLYTSYNQGI

GTLFRVTETIDGYNLINIQQNLNLLNSTKSIRLLNGAIYILKVEVTELNNYNIKLHIDITNGS

GGDDPPGSSERTFLPNGNYKIKSLFSDSLYLTYSSGALSFSNTSSDDNQKWKLEYISSSNGFR

FSNVAEPNKYLAYNDDGYIYLSSSSNNSLWNPIKIAINSYIICTLSIVNVTDYAWTIYDNNNN

ITDQPILNLPNFDINNSNQILKLEKLGSGSAWSHPQFEK

>linked-mini (2 + 3)/CB-YFDY/IC (SEQ ID NO: 51):
MASENIQEINTAISDNYTYNIPGIVNNNPFYILFTVNTTGIYKINAQNNLPSLKIYEAIGSGN

RNFQSGNLCDDDIKAINYITGFDSPNAKSYLVVLLNKDKNYYIRVPQTSSNIENQIKFKREEG

DLRNLMNSSVNIIDNLNSTGAHYYTRQSPDVHDYISYEFTIPGNFNNKDTSNIRLYISYNQGI

GTLFRVTETIDGYNLINIQQNLNLLNSTKSIRLLNGAIYILKVEVTELNNYNIKLHIDITNGS

GGDDPPGSSERTFLPNGNYKIKSLFSDSLYLTYSSGALSFSNTSSLDNQKWKLEYISSSNGFR

FSNVAEPNKYLAYNDDGYIYLSSSSNNSLWNPCKIAINSYTICTLSIVNVTDYAWTIYDNNNN

ITDQPILNLPNEDINNSNQILKLEKLGSGSAWSHPQFEK

>linked-mini (2 + 3)/CB-YFDY/ITCC (SEQ ID NO: 52):
MASENIQEINTAISDNYTYNIPGIVNNNPFYILFTVNTTGIYKINAQNNLPSLKIYEAIGSGN

RNFQSGNLCDDDIKAINYITGFDSPNAKSYLVVLLNKDKNYYIRVPQTSSNIENQIKFKREEG

DLRNLMNSSVNIIDNLNSTGAHYYTRQSPDVHDYISYEFTIPGNFNNKDTSNIRLYTSYNQGI

GTLFRVCETIDGYNLINIQQNLNLLNSTKSIRLINGAIYILKVEVIELNNYNIKLHIDITNGS

GGDDPPGSSERTFLPNGNYKIKSLFSDSLYLTYSSGALSFSNTSSLDNQKWKLEYISSSNGFR

FSNVAEPNKYLAYNDDGYIYLSSSSNNSLWNPCKIAINSYIICTLSIVNVIDYAWTIYDNNNN

ITDQPILNLPNFDINNSNQLKLEKLGSGSAWSHPQFEK (5) TER Test

1. Caco-2 cells were seeded in a collagen-coated transwell chamber with 0.4 μm-pore size 6.5 mm diameter [Costar], and cultured in Caco-2 cell culture medium (20% FBS [Equitech-Bio], MEM [Gibco], 1 mM L-glutamine [Gibco], 17.86 mM $NaHCO_3$ [Wako], 15 mM Hepes [Dojindo], pH 7.4, 70 U/ml penicillin G-70 ug/ml Streptomycin [Gibco]) in a $CO_2$ incubator (37° C., 5% $CO_2$).
2. The medium was changed every 3 days until the TER value reached 600 $\Omega \cdot cm^2$ or more.
3. Each transwell was washed with PBS the day before the test, and the cells were cultured overnight in the medium in a $CO_2$ incubator.
4. Each HA was added to 2 or 3 wells and to the basal side chamber of each well to a final concentration of 30-300 nM by protomer calculation, and cultured in a $CO_2$ incubator.

5. Until 24 hr after HA addition, the TER value of each well was measured over time using Millicell-ERS2 [Millipore].
6. The measurement values were calculated by the following formula, the mean of 2 or 3 wells was determined, and the standard deviation was taken as the error.

$$[TER^{calc\,(X\ hr)}] = ([TER^{X\ hr}]/[TER^{0\ hr}] \times 100$$

(6) Cytotoxicity Test

1. Caco-2 cells were seeded on a 96 well plate at 1×10^4 cell/well in a Caco-2 cell culture medium (100 µl/well), and cultured in a $CO_2$ incubator (37° C., 5% $CO_2$) for 24 hr.
2. A well containing a medium alone and without seeding of cells was used as a blank.
3. 1% Triton X-100 or various proteins were added to 3 wells each of a 96 well plate to a final concentration of 300 nM by protomer calculation, and cultured in a $CO_2$ incubator for 48 hr.
4. SF reagent [nacalai tesque] was added by 10 µl to each well, followed by culture for 1.5 hr.
5. 1% SDS was added by 10 µl to each well, and absorbance was measured at wavelength 450 nm and 620 nm.
6. The measurement values were calculated by the following formula.

$$A450^{calc\,(sample)} = ([A450^{sample}] - [A620^{sample}]) - ([A450^{blank}] - [A620^{blank}])$$

7. As the measurement value, an average of 3 wells was determined under respective conditions and standard deviation was taken as the error.

(7) Cell-Cell Adhesion Inhibitory Test

1. Human iPS cell D2 strain (obtained from: Center for iPS Cell Research and Application (CiRA), Kyoto University) precultured for 4 days on a 100 mm dish was seeded under feeder-free conditions at a density of $2.5\times10^3$ cells/cm$^2$ in a 48-well plate (costar 3548) with each well containing StemFit (registered trade mark) AK02N medium (200 µl) (Day0).
2. The 48-well plate was cultured in a $CO_2$ incubator at 5% $CO_2$ atmosphere at 37° C. for 3 days. The medium was changed every other day, various concentrations (0.1-450 nM) of linked-mini(2+3)/CB-LD/YFDY or FL-HA (HFHS) of type B were added to the wells (each concentration 2 wells) for 24 hr from the day of start of culture (Day1) to 2 days (Day2). On 1, 2 and 3 days from the start of culture, microscopic photograph (4×) was taken.

(8) Cell Proliferation Test (a) SF Assay

1. MDCK cells were seeded on a 96 well plate at $1\times10^4$ cells/well in a MDCK cell culture medium (100 µl/well), and cultured in a $CO_2$ incubator (37° C., 5% $CO_2$) for 24 hr.
2. FL-HA or linked-mini(2+3)/CB-LD/YFDY was added to 3 wells each of a 96 well plate to a final concentration of 1-300 nM, and cultured in a $CO_2$ incubator for 24 hr.
3. SF reagent [nacalai tesque] was added by 10 µl to each well, followed by culture in a $CO_2$ incubator for 1.5 hr.
4. 1% SDS was added by 10 µl to each well, and absorbance was measured at wavelength 450 nm and 620 nm.
5. The measurement values were calculated by the following formula.

$$A450^{calc\,(sample)} = ([A450^{sample}] - [A620^{sample}]) - ([A450^{blank}] - [A620^{blank}])$$

6. As the measurement value, an average of 3 wells was determined under respective conditions and standard deviation was taken as the error.

(b) Cell Number Measurement

1. MDCK cells were seeded on a 35 mm dish in an MDCK cell culture medium (1.5 ml/dish) at $1\times10^4$ cells/dish, and cultured in a $CO_2$ incubator (37° C., 5% $CO_2$) for 48 hr.
2. Each dish was washed with PBS, FL-HA at final concentration of 30 nM (protomer 90 nM) or linked-mini(2+3)/CB-LD/YFDY at a final concentration of 100 nM was added to 3 dishes each, and cultured in a $CO_2$ incubator for 48 hr.
3. Each dish was washed with PBS, 0.25% trypsin-EDTA [GIBCO] was added to the dish, of the dish was incubated in a $CO_2$ incubator for 30 min. Then, an FBS-containing medium was added to each dish and the cells were collected.
4. The number of cells was counted using a cell counter [One Cell].
5. As the number of cells, the average of 3 dishes was calculated in each group, and the standard deviation was taken as the error.

Figure 1:
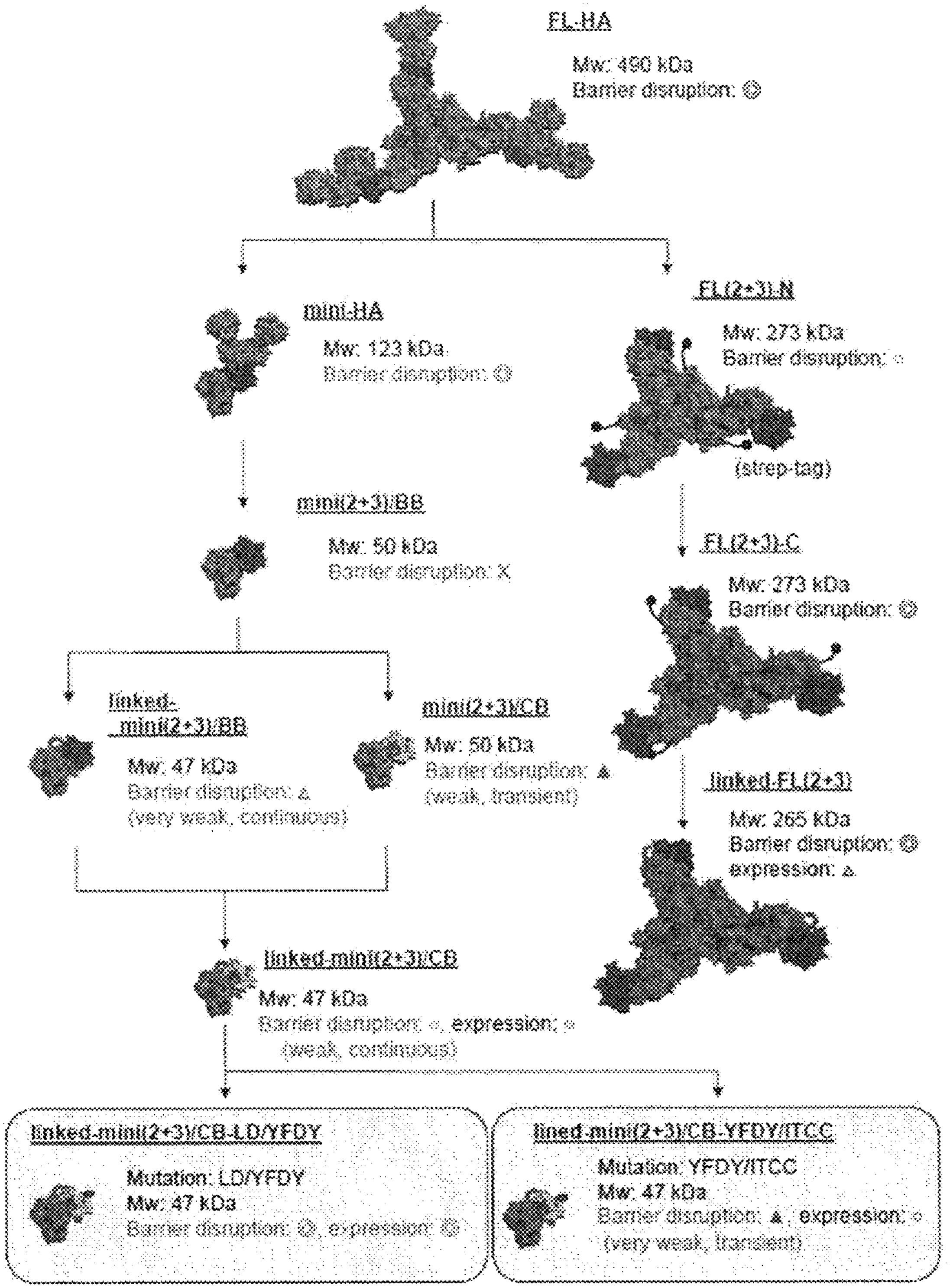
FIG. 1 is a flow diagram schematically showing the miniaturization strategy of the HA complex protein of the present invention.
Figure 2:
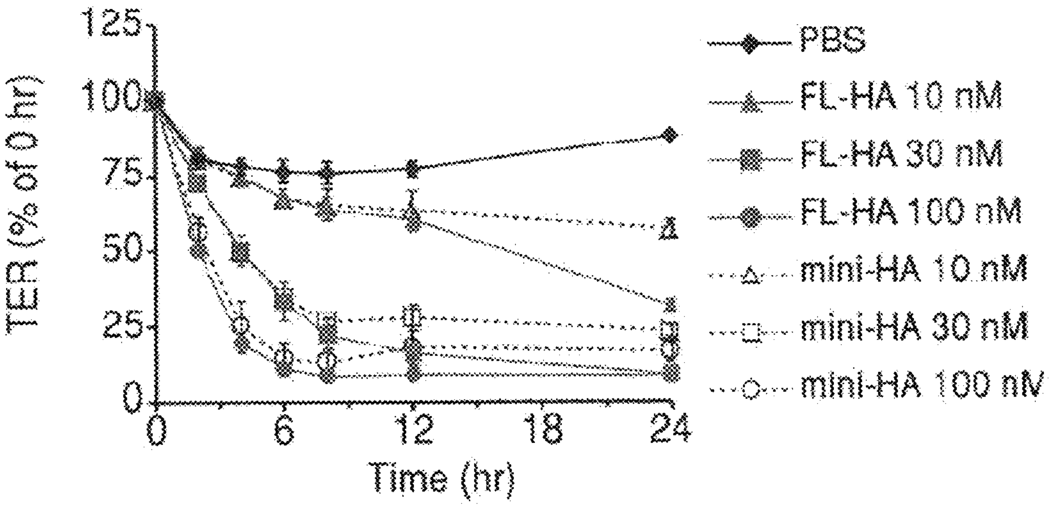
FIG. 2 is a drawing showing the effects of a mini-HA complex and a FL-HA complex on the TER value in cultured Caco-2 cells.

Results (1) The effects of various concentrations of whole HA 12-mer (FL-HA) and a monovalent HA complex lacking a part of HA3 (mini-HA) on the TER value of Caco-2 cells were examined. As a result, it was shown that mini-HA has cadherin function inhibitory activity similar to that of FL-HA (FIG. 2).

Figure 3:
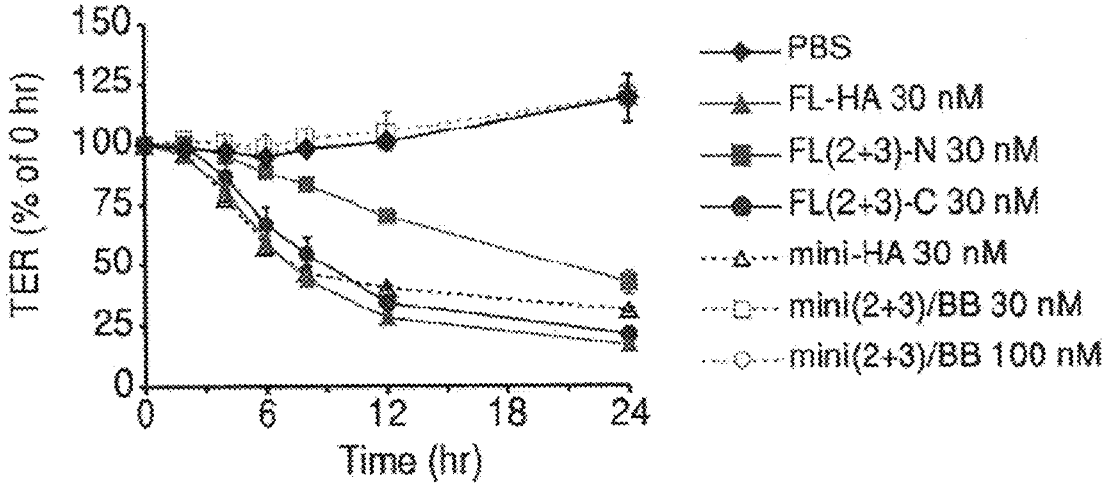
FIG. 3 is a drawing showing the effects of a mini(2+3) complex and a FL(2+3)-N and FL(2+3)-C complex on the TER value in cultured Caco-2 cells.

(2) The effects of various concentrations of trivalent, C-terminal or N-terminal-tagged complexes lacking HA1 subcomponent (FL(2+3)-C, FL(2+3)-N) on the TER value of Caco-2 cells were examined. As a result, when a tag was added to the N-terminal of the HA3 subcomponent, the cadherin function inhibitory activity decreased to about ⅓ of that of FL-HA. On the other hand, when the tag was added to the C-terminal of HA3 subcomponent, the cadherin function inhibitory activity was maintained at a level near that of FL-HA (FIG. 3).

(3) The effects of various concentrations of mini(2+3) lacking the HA1 subcomponent on the TER value of Caco-2 cells were examined. As a result, mini(2+3) did not have or showed very weak cadherin function inhibitory activity (FIG. 3).

Figure 4:
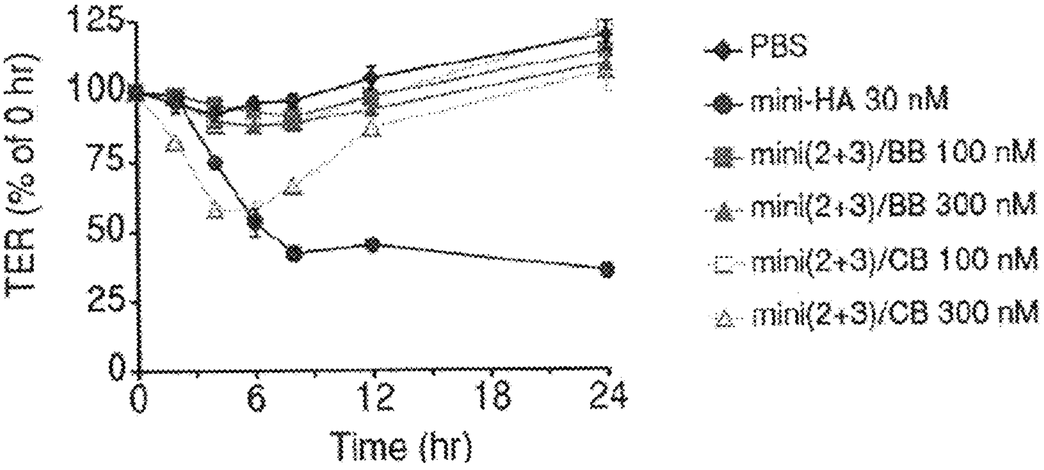
FIG. 4 is a drawing showing the effects of a mini(2+3)/BB complex and a mini(2+3)/CB complex on the TER value in cultured Caco-2 cells.
Figure 12:
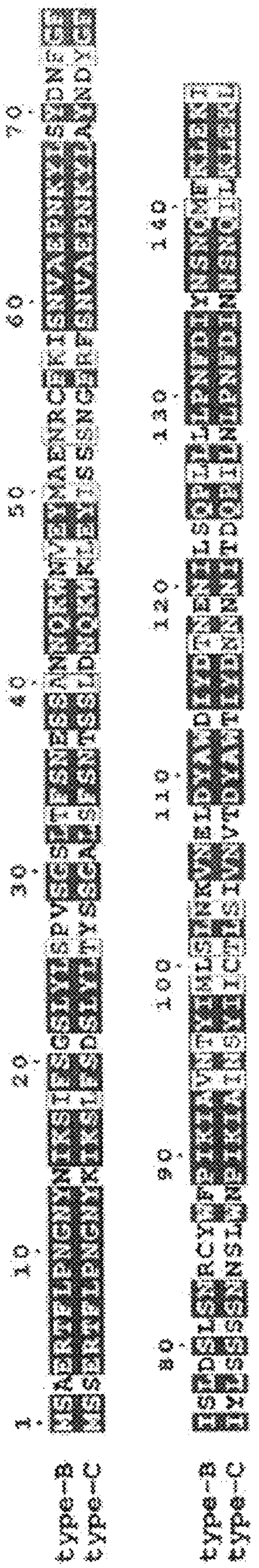
FIG. 12 is a drawing showing alignment of HA2 subcomponents of type B (SEQ ID NO: 4) and type C (SEQ ID NO: 5).

(4) In mini(2+3), the effects of various concentrations (concentration as protomer molecule) of mini(2+3)/CB having the HA2 subcomponent substituted by type C on the TER value of Caco-2 cells were examined (alignment of amino acid sequences HA2 of type B and HA2 of type C is shown in FIG. 12). As a result, it was clarified that cadherin function inhibitory activity was shown, though temporarily, by the use of the HA2 subcomponent of type C (FIG. 4).

Figure 5:
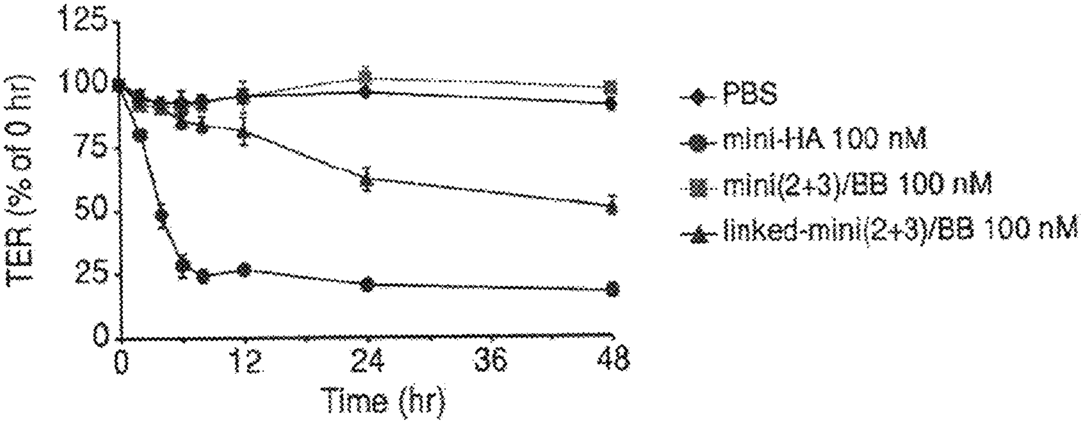
FIG. 5 is a drawing showing the effects of a mini(2+3)/BB complex and a linked-mini(2+3)/BB complex on the TER value in cultured Caco-2 cells.

(5) When the HA2 subcomponent and the HA3 subcomponent were linked via a linker (FIG. 13), mini(2+3)/BB showed cadherin function inhibitory activity even though the HA2 subcomponent was type B (FIG. 5).

Figure 6:
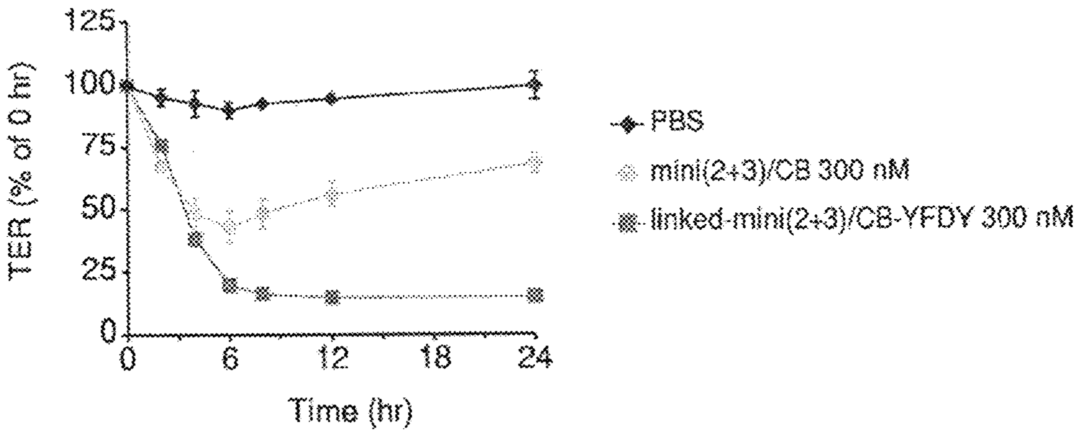
FIG. 6 is a drawing showing the effects of a mini(2+3)/CB complex and a linked-mini(2+3)/CB-YFDY complex on the TER value in cultured Caco-2 cells.
Figure 7:
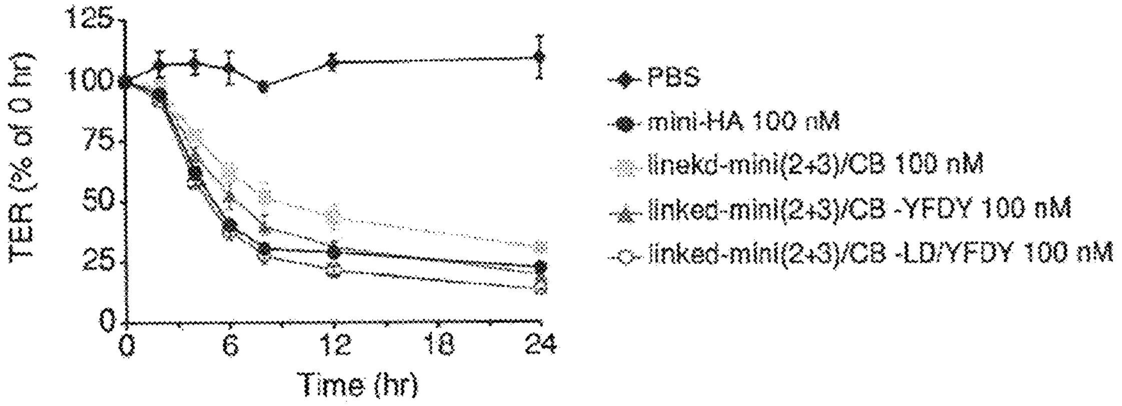
FIG. 7 is a drawing showing the effects of a linked-mini (2+3)/CB complex, a linked-mini(2+3)/CB-YFDY complex and a linked-mini(2+3)/CB-LD/YFDY complex on the TER value in cultured Caco-2 cells.

In mini(2+3)/CB, when the HA2 subcomponent and the HA3 subcomponent were linked via a linker, the cadherin function inhibitory activity changed from temporary to sustained one (FIG. 6, FIG. 7).

Figure 8:
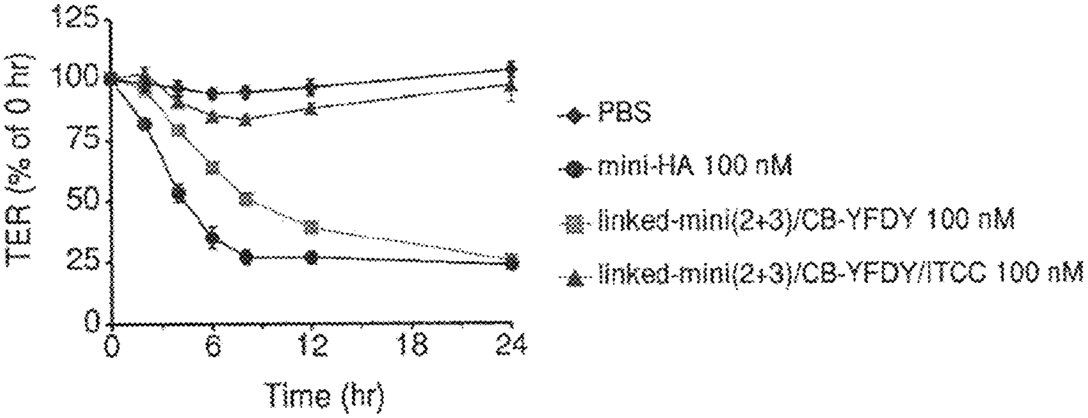
FIG. 8 is a drawing showing the effects of a linked-mini (2+3)/CB-YFDY complex and a linked-mini(2+3)/CB-YFDY/ITCC complex on the TER value in cultured Caco-2 cells.

(6) In linked-mini(2+3)/CB, various mutations shown in FIGS. 14 and 15 were introduced and change of cadherin function inhibitory activity was examined. As a result, when a mutation that replaces hydrophobic amino acid residues in the HA2 subcomponent with more hydrophilic amino acids was introduced [linked-mini(2+3)/CB-YFDY, linked-mini(2+3)/CB-LD/YFDY], the cadherin function inhibitory activity was further improved and activity equivalent to that of mini-HA was shown (FIG. 7). On the other hand, when a cysteine residue was introduced into each of the HA2 subcomponent and the HA3 subcomponent [linked-mini (2+3)/CB-YFDY/ITCC], the cadherin function inhibitory activity which became persistent with the use of linker changed to temporary one (FIG. 8).

Figure 11:
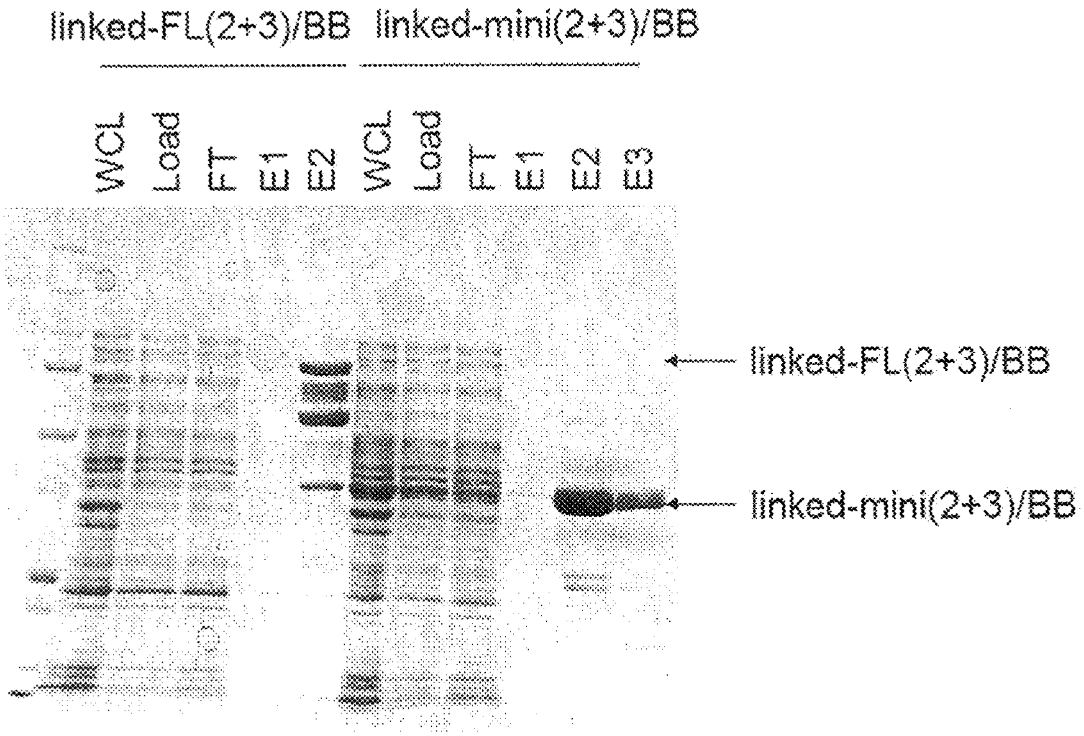
FIG. 11 is a drawing showing a comparison of a linked-mini(2+3) complex and a linked-FL(2+3) complex in the expression and purification.

(7) The HA2 subcomponent and the HA3 subcomponent were linked via a linker, a construct with strep tag added to the C-terminal of HA2 was introduced into *Escherichia coli* to allow for expression, and the culture medium was applied to StrepTrap to purify linked-mini(2+3)/BB. As a result, contaminants or decomposed products were often found in linked-FL (2+3)/BB but linked-mini(2+3)/BB could be purified at a high purity (FIG. 11).

When HA1, HA2 and HA3 subcomponents of type B were separately expressed, purified using a tag, mixed, incubated and reconstituted. By calculation with a constitution yield of 50-80% and conversion to culture of the total 3 L, 0.13-0.2 μmol was obtained with 3× protomer as 1 molecule, and 0.4-0.6 μmol as protomer. When HA2 and HA3 were linked via a linker, by conversion to culture of 3 L, 5.1 μmol of HA complex was obtained with linked-mini (2+3)/BB, 3.3 μmol of HA complex was obtained with linked-mini(2+3)/CB, and 8.4 μmol of HA complex was obtained with mutation-introduced linked-mini(2+3)/CB-YFDY, which was about 10 times higher yield per monovalent molecule.

Figure 9:
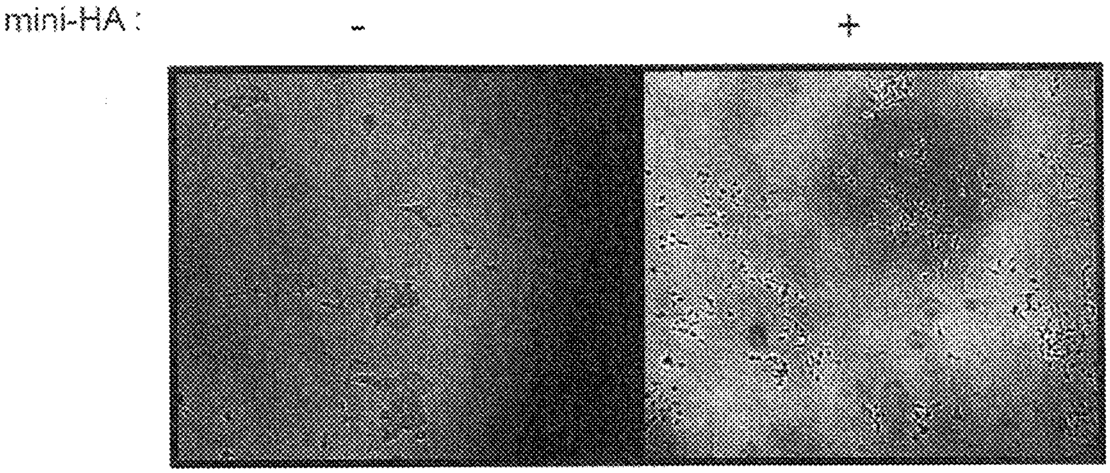
FIG. 9 is a drawing showing the effects of a mini-HA complex on the cell-cell adhesion of cultured MDCK cells.

(8) The mini-HA was added to the medium of MDCK cultured cells at a concentration of 100 nM and incubated. As a result, cell clumps in which some tens of cells were adhered were observed in the absence of mini-HA, whereas the cells were separated in the presence of mini-HA (FIG. 9).

Figure 10:
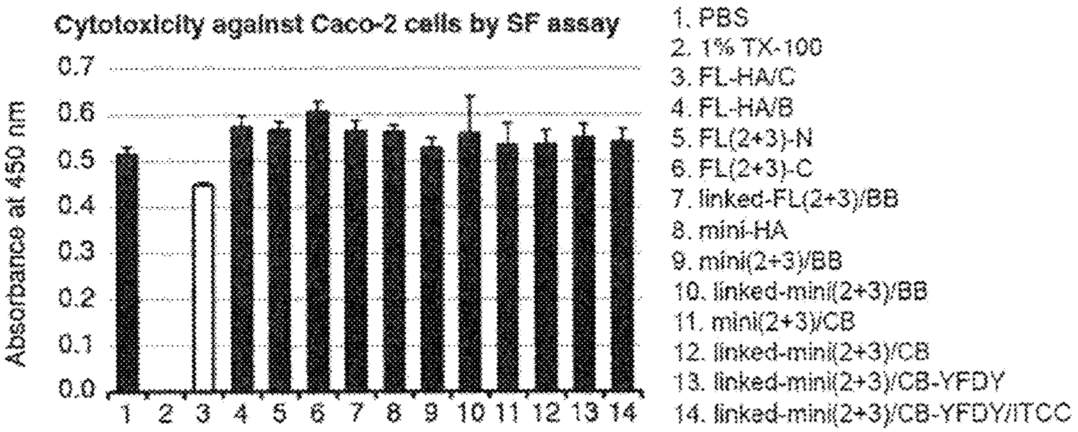
FIG. 10 is a drawing showing the results of a cytotoxicity test of various HA complex proteins against Coca-2 cells.

(9) Various HA complex proteins were added at a concentration of 300 nM as a protomer to the medium of Caco-2 cells, and cytotoxicity was examined. No cytotoxicity was observed in any of the HA complexes except that the cell viability decreased in C-type FL-HA, and rather, a tendency to support cell survival was found (FIG. 10).

Figure 16A:
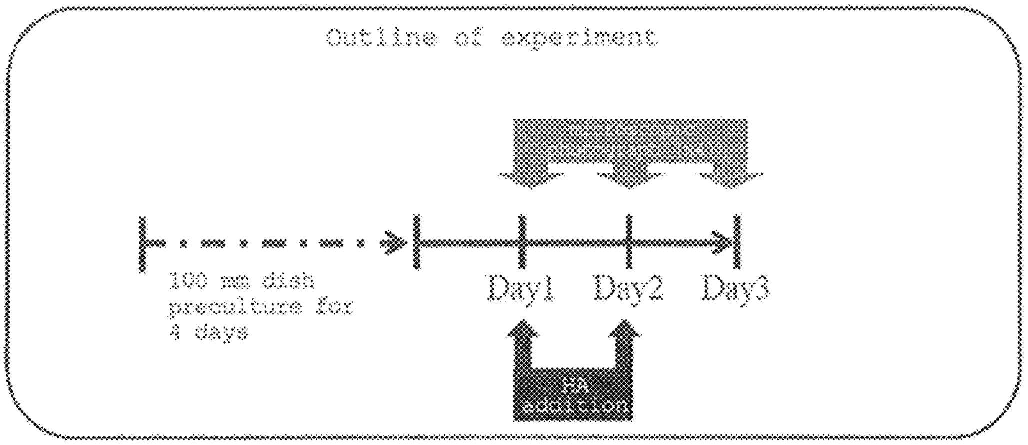
FIGS. 16A and 16B are a drawing showing the effects of a linked-mini(2+3)/CB-LD/YFDY complex on the cell-cell adhesion of iPS cells.
Figure 16B:
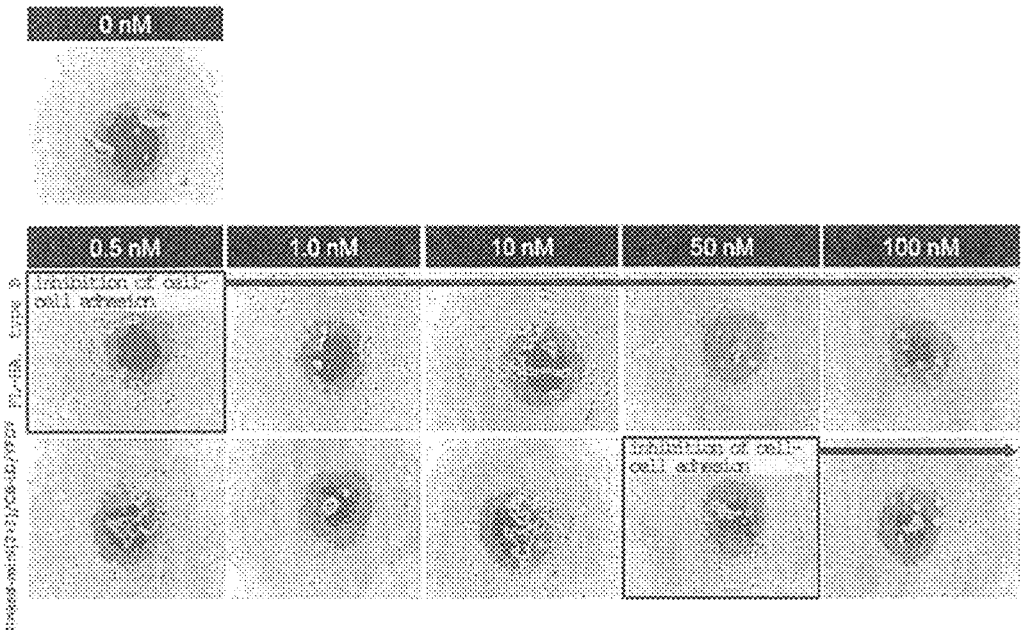

(10) Human iPS cell D2 strain was cultured for 3 days, linked-mini (2+3)/CB-LD/YFDY or FL-HA of type B was added to the medium for 24 hr from day 1 (Day1) to day 2 (Day2) from the start of culture, and changes in the cell form during culture were comparison observed. As a result, as shown in FIG. 16B, it was clarified that the addition of linked-mini(2+3)/CB-LD/YFDY inhibits cell-cell adhesion of iPS cell clump as with FL-HA. The linked-mini(2+3)/CB-LD/YFDY showed the cell-cell adhesion inhibitory effect at a concentration of not less than 50 nM (FIG. 16B shows only the results at 0.5-100 nM; however, the cell-cell adhesion inhibitory effect was shown without cytotoxicity even at higher concentrations (up to 450 nM)).

Figure 17:
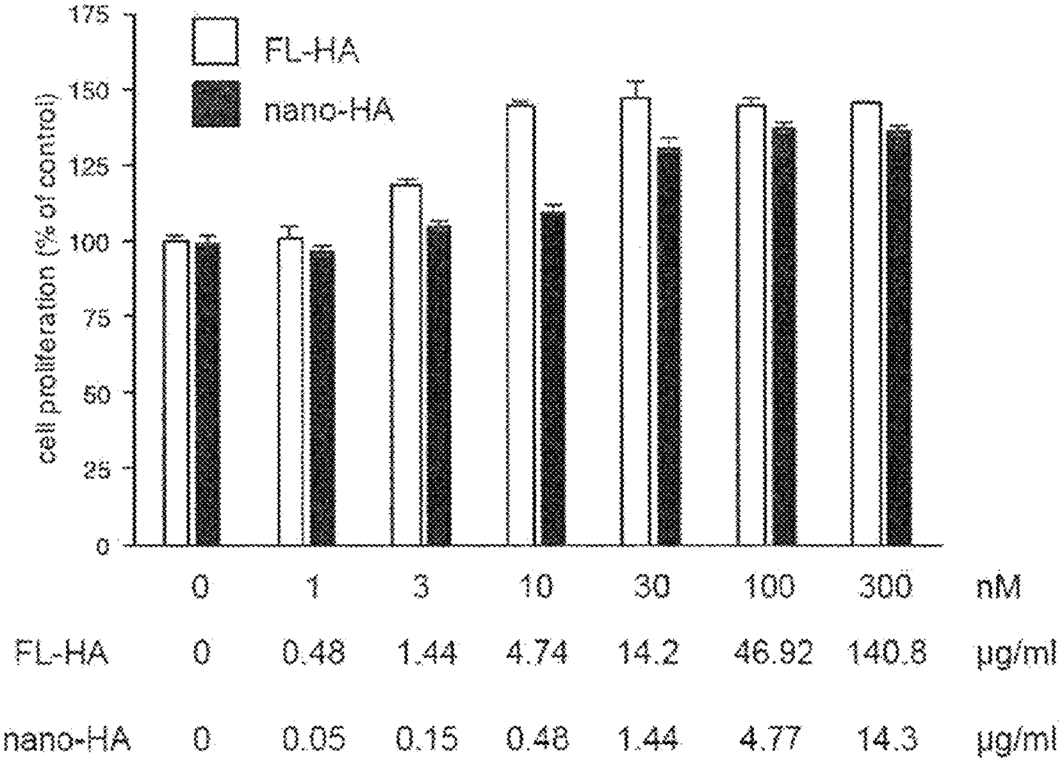
FIG. 17 is a drawing showing the effects of various concentrations of an FL-HA complex (FL-HA) of type B and a linked-mini(2+3)/CB-LD/YFDY complex (nano-HA)

(11) By an SF assay, the MDCK cell proliferation promoting action of various concentrations (1-300 nM) of FL-HA and linked-mini(2+3)/CB-LD/YFDY was analyzed. As a result, the linked-mini(2+3)/CB-LD/YFDY showed a remarkable cell proliferation promoting action at not less than 30 nM, and showed about ⅓ of the effect as compared to the same molar concentration of FL-HA (single-arm: equivalent per protomer) (FIG. 17). Since the molecular weight of the linked-mini(2+3)/CB-LD/YFDY was about 1/10 that of FL-HA, when converted to a weight/volume concentration, the linked-mini(2+3)/CB-LD/YFDY showed about 3 times stronger activity as compared to FL-HA (FIG. 17).

(12) The proliferation promoting effect of HA in MDCK cells was analyzed by counting the number of the cells. As a result, the linked-mini(2+3)/CB-LD/YFDY showed a proliferation-promoting effect comparable to FL-HA at an equivalent molar concentration per single-arm (protomer) (FIG. 18). When converted to a weight/volume concentration, it showed about 3 times stronger activity as compared to FL-HA.

INDUSTRIAL APPLICABILITY

The HA complex protein of the present invention is miniaturized while maintaining the cadherin function inhibitory activity. Thus, the HA complex protein is advantageous over conventional products because it simplifies the production step and is easy to handle. In addition, it is low toxic and has a cell proliferation promoting action. Therefore, it is extremely useful as, for example, a medium additive for maintaining an undifferentiated state of pluripotent stem cells including iPS cells and promoting cell proliferation.

This application is based on a patent application No. 2017-226370 filed in Japan (filing date: Nov. 24, 2017), the contents of which are incorporated in full herein.

The invention claimed is:

1. A nucleic acid encoding a miniaturized hemagglutinin complex protein, wherein the miniaturized hemagglutinin complex protein has function inhibitory activity against E-cadherin, and wherein the miniaturized hemagglutinin complex protein is selected from the group consisting of:

(1) mini-HA consisting of HA1 subcomponent of SEQ ID NO: 10, HA2 subcomponent of SEQ ID NO: 4, and HA3 subcomponent fragment of SEQ ID NO: 2, (2) FL(2+3)-C consisting of HA2 subcomponent of SEQ ID NO: 4 and HA3 component with Strep-Tag (C-terminus) of SEQ ID NO: 44, (3) linked-mini(2+3)/BB of SEQ ID NO: 47, (4) linked-mini(2+3)/CB of SEQ ID NO: 48, (5) linked-mini(2+3)/CB-YFDY of SEQ ID NO: 49, and (6) linked-mini(2+3)/CB-LD/YFDY of SEQ ID NO: 50.

2. A method for producing a hemagglutinin complex protein comprising:

culturing a host cell into which the expression vector comprising the nucleic acid according to claim 1, collecting a hemagglutinin complex protein or a subcomponent thereof from the obtained culture, in the case of the subcomponent, further contacting the obtained subcomponents with each other and collecting the hemagglutinin complex protein produced thereby.

* * * * *